(12) United States Patent
Otvos

(10) Patent No.: US 6,576,471 B2
(45) Date of Patent: Jun. 10, 2003

(54) METHODS, SYSTEMS, AND COMPUTER PROGRAM PRODUCTS FOR ANALYZING AND PRESENTING NMR LIPOPROTEIN-BASED RISK ASSESSMENT RESULTS

(75) Inventor: James D. Otvos, Apex, NC (US)

(73) Assignee: LipoScience, Inc., Raleigh, NC (US)

( * ) Notice: Subject to any disclaimer, the term of this patent is extended or adjusted under 35 U.S.C. 154(b) by 0 days.

(21) Appl. No.: 09/992,068

(22) Filed: Nov. 14, 2001

(65) Prior Publication Data

US 2002/0087276 A1 Jul. 4, 2002

Related U.S. Application Data

(60) Division of application No. 09/291,736, filed on Apr. 14, 1999, now abandoned, which is a continuation-in-part of application No. 09/258,740, filed on Feb. 26, 1999.

(51) Int. Cl.$^7$ .............................................. G01N 33/92
(52) U.S. Cl. ............................. 436/71; 436/13; 436/16; 436/173
(58) Field of Search ............................. 436/13, 16, 71, 436/173; 600/300; 128/630

(56) References Cited

U.S. PATENT DOCUMENTS

| | | | | |
|---|---|---|---|---|
| 4,464,122 A | * | 8/1984 | Fuller et al. | 283/115 |
| 4,933,844 A | | 6/1990 | Otvos | 364/413.08 |
| 5,343,389 A | | 8/1994 | Otvos | 364/413.09 |
| 5,385,828 A | | 1/1995 | Aufenanger | 435/11 |
| 5,396,886 A | | 3/1995 | Cuypers | 600/301 |
| 5,692,501 A | * | 12/1997 | Minturn | 600/301 |
| 5,724,580 A | | 3/1998 | Levin et al. | 395/615 |

FOREIGN PATENT DOCUMENTS

| | | |
|---|---|---|
| WO | WO 91/10128 | 7/1991 |
| WO | WO 93/03450 | 2/1993 |

OTHER PUBLICATIONS

News Release, *Radio signals give new spectrum for cholesterol lipoprotein readings*, American Heart Association Journal Report (Jul. 9, 1998).

Brochure, *New Technology Detects Hidden Risk of Heart Disease; NMR Lipoprofile™ Seen as Powerful New Tool in Disease Assessment and Management*, LipoMed, Inc., Raleigh, NC (Mar. 26, 1998).

Abstracts, Supplement to Circulation, Journal of the American Heart Association Abstracts for the 71st Scientific Sessions (11/98).

Otvos, *Measurement of Lipoprotein Subclass Profiles by NMR Spectroscopy*, Handbook of Lipoprotein Testing, pp. 497–508 (AACC Press, 1997).

(List continued on next page.)

Primary Examiner—Jill Warden
Assistant Examiner—Yelena Gakh
(74) Attorney, Agent, or Firm—Myers Bigel Sibley & Sajovec PA

(57) ABSTRACT

A method for analyzing a patient's risk of coronary heart disease by determining the presence of NMR-derived or based lipoprotein constituent value abnormalities includes determining the presence of atherogenic dyslipidemia based on the existence of a clustering of lipoprotein constituent abnormalities as defined by predetermined test criteria. Computer program products and automatically produced reports for presenting NMR-derived lipoprotein risk assessment based on patient-specific lipoprotein subclass results present the measurement results adjacent to a segmented reference risk analysis portion. The actual measured results are visually aligned and enhanced within the risk analysis portion to provide easy reference and understanding of the results relative to a risk of developing coronary heart disease.

49 Claims, 17 Drawing Sheets

OTHER PUBLICATIONS

Freedman et al., *Relation of Lipoprotein Subclasses as Measured by Proton Nuclear Magnetic Resonance Spectroscopy to Coronary Artery Disease, Arterioscler Thromb Vasc Biol. 18*, pp. 1046–1053 (Jul. 1998).

Wilson et al., *Prediction of Coronary Heart Disease Using Risk Factor Categories*, American Heart Association, Inc. pp. 1837–1847 (5/98).

National Cholesterol Education Program, "Second Report of the Expert Panel on Detection, Evaluation, and Treatment of High Blood Cholesterol in Adults (Adult Treatment Panel II)," Circulation 1994, vol. 89, No. 3 (pp. 1329–1445 (Mar. 1994).

Lamarche et al., "Apolipoprotein A–I and B Levels and the Risk of Ischemic Heart Disease During a Five–Year Follow–up of Men in the Québec Cardiovascular Study," Circulation, vol. 94, No. 3, pp. 273–278 (Aug. 1, 1996).

Wilson, et al., "Impact of National Guidelines for Cholesterol Risk Factor Screening," JAMA, vol. 262, No. 1, pp. 41–44 (Jul. 7, 1989).

Press Release, "Size Matters—When it Comes to Cholesterol Particles and Heart Disease Risk," LipoMed, Inc., Raleigh, NC (Apr. 14, 1999).

Brochure, "NMR LipoProfile™", LipoMed, Inc., Raleigh, NC (on or about Mar. 28, 1998).

"Magnetic Resonance Test May Give Better Assessment of Heart Disease Risk," Doctor's Guide, Online pp. 1–3 url:http://www.pslgroup.com/dg8DE5A.htm (Jun. 8, 2000).

"Company Profile: LipoMed Technology Anticipated to be a Leading Predictor of Heart Disease," BT Catalyst, Online, pp. 1–3, url:htt;"//www.ncbiotech.org/feb98–4.hum (Jun. 8, 2000).

"New Test More Accurately Measures Risk of Heart Disease, Study Finds," NC State University Document View, Online, pp. 1–6 (Jul. 13, 1998, url:http://search.ncsu.edu (Jun. 8, 2000).

Ala–Korpela et al., "Quantification of Biomedical NMR Data Using Artificial Neural Network Analysis: Lipoprotein Lipid Profiles from $^1$H NMR Data of Human Plasma," NMR in Biomedicine, GB, Wiley, London, vol. 8, No. 6, pp. 235–244 (Sep. 1, 1995).

PCT International Search Report, International Application No. PCT/US99/29730, mailed Jul. 6, 2000.

Chapman et al., "Atherogenic, dense low–density lipoproteins," Eur. Heart J. 1998, 19, Suppl A, A24–30.

Griffin et al., "Role of plasma triglyceride in the regulation of plasma low density lipoprotein (LDL) . . . ," Atherosclerosis 1994, 106(2), 241–53.

Campos et al., "LDL particle size distribution . . . " Arterioscler Tromb 1992, 12 (12), pp. 1410–1419.

Krauss, "Relationship of intermediate and low–density lipoprotein . . . ," Am. Heart J. 1987, 113 (2Pt2), 5780–82.

Rapp et al., "Particle size distribution . . . ," J. Vasc. Surgery, 1989, 9 (1), 81–88.

Ala–Korpela et al., "A comparative study of 1H NMR lineshape . . . ," NMR Biomed, 1993, 6, 225–233.

Jones PH, "Clinical diagnosis of lipid disorders," Clin. Cornerstone, 1998, 1 (1), pp. 15–30.

Miwa et al., "High–density lipoprotein particles are large in . . . ," Cardiovasc. Res., 1998, 37 (3), pp. 729–737.

* cited by examiner

Summary Report

Patient Name: Jane Doe
Patient ID: RP21-3947
Physician Name & Address:
Phone: ( )
FAX: ( )
Comments:

| Specimen ID | Date Collected | Date Received | Date Reported |
|---|---|---|---|
| LM99-1402 | 01-25-99 | 01-26-99 | 01-27-99 |

| Sex | Age | Blood Pressure | Diabetes | Smoker |
|---|---|---|---|---|
| F | 53 | 132/86 | No | Yes |

LIPID PROFILE*

Current NCEP Guidelines for Primary Prevention

| | mg/dL | Desirable | Borderline-High | High |
|---|---|---|---|---|
| Total Cholesterol | 230 | less than 200 | 200-239 | 240 or greater |
| LDL Cholesterol | 165 | less than 130 | 130-159 | 160 or greater |
| HDL Cholesterol | 42 | Negative Risk Factor: 60 or greater | Intermediate: 35-59 | Positive Risk Factor: less than 35 |
| Triglycerides | 160 | Desirable: less than 200 | Borderline-High: 200-400 | High: 400-1,000 |

* Lipid profile values are derived from direct NMR measurement of plasma lipoproteins, not from standard lipid tests. For most patients, NMR and standard lipid panel values agree closely. Some patients with metabolic abnormalities or elevated triglycerides have abnormally cholesterol-poor LDL particles. Their LDL cholesterol levels when measured by standard tests will be lower than determined by NMR. The NMR values more closely reflect the actual number of LDL particles in the circulation.

SUBCLASS PROFILE

| | nm | Pattern A (large) | Pattern AB (Intermediate) | Pattern B (small) |
|---|---|---|---|---|
| LDL Size | 19.6 | 20.6-22.0 | 20.4-20.5 | 19.0-20.3 |
| | | Lower-Risk | | Higher-Risk |

| | | Percentage of population with a lower level |
|---|---|---|
| LDL Particles | 2205 nmol/L | (94%) Lower ← CHD Risk → Higher |
| Large HDL Cholesterol | 21 mg/dL | (71%) Percentage of population with a higher level — Lower ← CHD Risk → Higher |
| Large VLDL Trygyceride | 30 mg/dL | (78%) Percentage of population with a lower level — Lower ← CHD Risk → Higher |

Population percentages are based on data obtained from analysis of 3,437 subjects in the Framingham Offspring Study.

FIG. 1

Risk Assessment Report — 10'

| Patient Name | Specimen ID | Date Reported |
|---|---|---|
| Jane Doe | LM99-1402 | 01-27-99 |

Supplemental Risk Factors — 50

CHD risk can increase significantly when there is a clustering of metabolic abnormalities not detected by standard lipid tests. A check mark in multiple boxes below suggests the patient has a metabolic profile associated with a higher level of risk.

| Risk Factor | Result | Description |
|---|---|---|
| Small LDL | Pattern B ✓ | Small LDL (Pattern B) is a hallmark of the "atherogenic lipoprotein phenotype" and confers about 3 to 4-fold higher risk compared to the large LDL trait (Pattern A). Evidence suggests that small LDL particles may be inherently more atherogenic than large LDL. |
| Elevated Number of LDL Particles | Upper 33% ✓ | Unlike LDL cholesterol, LDL particle concentration (related closely to plasma apo B level), may be the single best indicator of LDL-associated CHD risk (Lamarche et al., Circulation 1996;94:273-278) and the best target of risk reduction therapy. |
| Low Level of Large HDL | Lower 33% ✓ | Only the larger HDL subclasses appear to be protective, whereas small HDL is positively associated with CHD (Freedman et al., Arterioscler Thromb Vasc Biol. 1998;18:1046-53). Large HDL, rather that total HDL cholesterol, may thus be a more sensitive risk factor. |
| Elevated Level of Large VLDL | Lower 33% ✓ | Elevated levels of large, triglyceride-rich VLDL particles have been associated with CAD severity, independently of plasma triglycerides. High concentrations of large VLDL in fasting plasma may be a marker for delayed chylomicron clearance (postprandial lipemia). |

Subclass Levels — 60

Subclass levels in mg/dL are given in parentheses above each bar. Bar height gives percent of population with lower levels.

VLDL Subclasses (mg/dL Triglyceride): Large VLDL (30), Medium VLDL (74), Small VLDL (4)

LDL Subclasses (mg/dL Cholesterol): IDL (9), Large LDL (31), Medium LDL (15), Small LDL (110)

HDL Subclasses (mg/dL Cholesterol): Large HDL (21), Small HDL (21)

Primary Prevention Risk Assessment — 70

Employs the Framingham algorithm in *Circulation* 1998;97:1837-1847

Given below is the patient's Framingham risk score and the estimated 10-year risk of developing CHD. Also given is the desirable low-level risk for the same age. Risk reduction should focus on modifying the starred risk factors.

Risk Factor Chart — 71

| Risk Factor | Relative Risk | Points |
|---|---|---|
| Age (53) | | 6 |
| * LDL-C (165) | High | 2 |
| * HDL-C (42) | High | 2 |
| Blood Pressure (132/86) | Moderate | 0 |
| Diabetes (No) | Low | 0 |
| * Smoker (Yes) | High | 2 |
| | Point Total | 12 |

Risk of Coronary Heart Disease — 72

| Point Total | 10-Year CHD Risk | Point Total | 10-Year CHD Risk | Point Total | 10-Year CHD Risk |
|---|---|---|---|---|---|
| ≤-2 | 1% | 6 | 6% | 12 | 15% |
| -1,0,1 | 2% | 7 | 7% | 13 | 17% |
| 2 | 3% | 8 | 8% | 14 | 20% |
| 3 | 3% | 9 | 9% | 15 | 24% |
| 4 | 4% | 10 | 11% | 16 | 24% |
| 5 | 5% | 11 | 13% | ≥17 | ≥32% |

Patient's Risk: 15%   Projected Risk at Age 60: 20%
Desirable Risk: 6%    Desirable Risk at Age 60: 8%

— 73: Desirable risk is calculated for a non-smoking, non-diabetic woman the same age, with optimal blood pressure (<120/80), LDL cholesterol 100-129 mg/dL, and HDL cholesterol 55 mg/dL. Projected risk at age 60 assumes patient's risk factors do not change.

FIG. 2

Risk Assessment Report

| Patient Name | Specimen ID | Date Reported |
|---|---|---|
| John Doe | LM99-3201 | 01-27-99 |

Supplemental Risk Factors

CHD risk can increase significantly when there is a clustering of metabolic abnormalities not detected by standard lipid measurements. Check marks in multiple boxes signify the presence of a metabolic profile associated with a higher level of risk than indicated by the LDL cholesterol value.

Small LDL — Pattern B [✓] — Small LDL (Pattern B) is a hallmark of the "atherogenic lipoprotein phenotype" and confers approximately 3-fold higher risk compared to the large LDL trait (Pattern A). Evidence suggests that small LDL particles may be inherently more atherogenic than large LDL.

Elevated Number of LDL Particles — Upper 33% [✓] — Unlike LDL cholesterol, LDL particle concentration (related closely to plasma apo B level), may be the single best indicator of LDL-associated CHD risk (Lamarche et al., Circulation 1998;94:273-278) and the best target of risk reduction therapy.

Low Level of Large HDL — Lower 33% [✓] — Only the larger HDL subclass particles appear to protect against CHD, whereas small HDL may even be atherogenic (Freedman et al., Arterioscler Thromb Vasc Biol. 1998;18:1048-53). Large HDL, rather than total HDL cholesterol, may thus be a more sensitive risk factor.

Elevated Level of Large VLDL — Upper 33% [✓] — Elevated levels of large, triglyceride-rich VLDL particles appear to be associated with CAD severity, independently of plasma triglycerides. High concentrations of large VLDL in fasting plasma may be a marker for delayed chylomicron clearance (postprandial lipemia).

Primary Prevention Risk Assessment — Employs the Framingham algorithm in Circulation 1998;97:1837-1847

Given below is the patient's Framingham risk score, the estimated absolute 10-year risk of developing CHD, and the desirable risk level for the same age. Risk reduction should focus on modifying the starred risk factors.

Risk Chart

| Risk Factor | Relative Risk | Points |
|---|---|---|
| Age (46) |  | 2 |
| * LDL-C (198) | Very High | 2 |
| * HDL-C (41) | High | 1 |
| * Blood Pressure (135/91) | High | 2 |
| Diabetes (No) | Low | 0 |
| * Smoker (Yes) | High | 2 |
| Point Total |  | 9 |

Absolute 10-Year CHD Risk

| Point Total | 10-Year CHD Risk | Point Total | 10-Year CHD Risk |
|---|---|---|---|
| ≤-3 | 1% | 6 | 11% |
| -2 | 2% | 7 | 14% |
| -1 | 2% | 8 | 18% |
| 0 | 3% | 9 | 22% |
| 1 | 4% | 10 | 27% |
| 2 | 4% | 11 | 33% |
| 3 | 5% | 12 | 40% |
| 4 | 7% | 13 | 47% |
| 5 | 9% | ≥14 | ≥56% |

Desirable Risk for Same Age: 4%

The desirable risk is calculated for a non-smoking, non-diabetic man the same age, with optimal blood pressure (<120/80), LDL cholesterol 100-129 mg/dL, and HDL cholesterol 45 mg/dL.

Secondary Prevention Guidelines

Patients with established CHD, other atherosclerotic vascular disease, or diabetes are considered to be at particularly high risk by the NCEP. The primary goal of lipid management should be the reduction of LDL cholesterol to under 100 mg/dL. The corresponding NMR LDL particle concentration target is 1100 nmol/L. For patients with a small LDL (pattern B) and a clustering of the supplemental risk factors shown above, it is especially important to reach these LDL goals. Smoking cessation, increased exercise, healthy diet, and blood pressure control are also important treatment goals.

FIG. 2A

Supplemental Risk Factors

CHD risk can increase significantly when there is a clustering of metabolic abnormalities not detected by standard lipid tests. A check mark in multiple boxes below suggests the patient has a metabolic profile associated with a higher level of risk.

Small LDL ☑ Pattern B — Small LDL (Pattern B) is a hallmark of the "atherogenic lipoprotein phenotype" and confers about 3 to 4-fold higher risk compared to the large LDL trait (Pattern A). Evidence suggests that small LDL particles may be inherently more atherogenic than large LDL.

Elevated Number of LDL Particles ☑ Upper 33% — Unlike LDL cholesterol, LDL particle concentration (related closely to plasma apo B level), may be the single best indicator of LDL-associated CHD risk (Lamarche et al., Circulation 1996;94:273-278) and the best target of risk reduction therapy.

Low Level of Large HDL ☑ Lower 33% — Only the larger HDL subclasses appear to be protective, whereas small HDL is positively associated with CHD (Freedman et al., Arterioscler Thromb Vasc Biol. 1998;18:1046-53). Large HDL, rather than total HDL cholesterol, may thus be a more sensitive risk factor.

Elevated Level of Large VLDL ☑ Upper 33% — Elevated levels of large, triglyceride-rich VLDL particles have been associated with CAD severity, independently of plasma triglycerides. High concentrations of large VLDL in fasting plasma may be a marker for delayed chylomicron clearance (postprandial lipemia).

FIG. 5

Primary Prevention Risk Assessment — Employs the Framingham algorithm in *Circulation* 1998;97:1837-1847

Given below is the patient's Framingham risk score and the estimated 10-year risk of developing CHD. Also given is the desirable low-level risk for the same age. Risk reduction should focus on modifying the starred risk factors.

Risk Factor Chart

| Risk Factor | Relative Risk | Points |
|---|---|---|
| Age (53) | | 6 |
| * LDL-C (165) | High | 2 |
| * HDL-C (42) | High | 2 |
| Blood Pressure (132/86) | Moderate | 0 |
| Diabetes (No) | Low | 0 |
| * Smoker (Yes) | High | 2 |
| | Point Total | 12 |

Risk of Coronary Heart Disease

| Point Total | 10-Year CHD Risk | Point Total | 10-Year CHD Risk | Point Total | 10-Year CHD Risk |
|---|---|---|---|---|---|
| ≤-2 | 1% | 6 | 6% | 12 | 15% |
| -1,0,1 | 2% | 7 | 7% | 13 | 17% |
| 2 | 3% | 8 | 8% | 14 | 20% |
| 3 | 3% | 9 | 9% | 15 | 24% |
| 4 | 4% | 10 | 11% | 16 | 24% |
| 5 | 5% | 11 | 13% | ≥17 | ≥32% |
| Patient's Risk | 15% | | | Projected Risk at Age 60 | 20% |
| Desirable Risk | 6% | | | Desirable Risk at Age 60 | 8% |

Desirable risk is calculated for a non-smoking, non-diabetic woman the same age, with optimal blood pressure (<120/80), LDL cholesterol 100-129 mg/dL, and HDL cholesterol 55 mg/dL. Projected risk at age 60 assumes patient's risk factors do not change.

FIG. 7

| Positive Risk Factor Chart | Relative Risk | Points |
|---|---|---|
| HDL-C ≥ 60 | Negative | -1 |
| LDL Size Pattern A | Negative | -2 |
| Elevated Large HDL | Negative | -1 |
| Exercise | Negative | -1 |

FIG. 7A

Secondary Prevention Guidelines
Patients with established CHD, other atherosclerotic vascular disease, or diabetes are considered to be at particularly high risk by the NCEP. The primary goal of lipid management should be the reduction of LDL cholesterol to under 100 mg/dL. The corresponding NMR LDL particle concentration target is 1100 nmol/L. For patients with small LDL (pattern B) and a clustering of the supplemental risk factors shown above, it is especially important to reach these LDL goals. Smoking cessation, increased exercise, healthy diet, and blood pressure control are also important treatment goals.

FIG. 8

NMR LipoProfile™ Summary Report /10'''

| Patient Name | Sex | Age | Physician Name & Address |
|---|---|---|---|
| Patient #5 | | | |

| Patient ID | Birth Date | Specimen ID | |
|---|---|---|---|
| | | LP001141 | Phone: ( )<br>FAX: ( ) |

| Data Collected | Data Received | Date Reported | Comments |
|---|---|---|---|
| | 04-02-99 | 04-05-99 | |

LIPID PROFILE /30'

Current NCEP Risk Categories

| | mg/dL | Desirable /36a | Borderline-High /36b | High /36c |
|---|---|---|---|---|
| Total Cholesterol /31' | 219 /31a' /31b | less than 200 | 200-239 | 240 or greater |

| | mg/dL /32b | Optimal* /36d | Desirable /36 | Borderline-High /36 | High Risk /36 |
|---|---|---|---|---|---|
| LDL Concentration /32'<br>(cholesterol equivalents) | 142 /32a' | less than 100 | 100-129 | 130-159 | greater than 160 |

| | mg/dL /33b | Negative Risk Factor /36 | Intermediate /36 | Positive Risk Factor |
|---|---|---|---|---|
| HDL Concentration /33'<br>(cholesterol equivalents) | 32 /33a' | 60 or greater | 59-35 | less than 35 |

| | mg/dL /34b | Desirable /36 | Borderline-High /36 | High /36 |
|---|---|---|---|---|
| Triglycerides /34' | 330 /34a' | less than 200 | 200-400 | 400-1,000 |

Lipid profile values are determined by measuring plasma lipoprotein levels directly by NMR, and converting concentrations to cholesterol or triglyceride units assuming that each lipoprotein has a normal lipid composition. For most patients, NMR and standard lipid panel values agree closely. Patients with certain metabolic abnormalities or elevated triglycerides may have cholesterol-depleted LDL. In these cases, LDL concentrations determined by NMR will be higher than those inferred by standard LDL cholesterol tests.

SUBCLASS PROFILE /40'

| | nmol/L /42b' | Optimal* | Desirable | Borderline-High /146 | High Risk |
|---|---|---|---|---|---|
| LDL Particles /42' | 1925 /42a' | less than 1100 | 1100-1399 | 1400-1799 | greater than 1800 |

| | nm /41b' | Pattern A (large LDL) | Intermediate Size | Pattern B (small LDL) |
|---|---|---|---|---|
| LDL Size /41' | 19.5 /41a' | 20.6-22.0 | 20.5-20.4 | 20.3-19.0 |
| | | Lower-Risk | | Higher-Risk |

| | mg/dL /43b' | Negative Risk Factor | Intermediate | Positive Risk Factor |
|---|---|---|---|---|
| Large HDL /43'<br>(cholesterol) | 11 /43a' | greater than 42 | 42-18 | less than 18 |

| | mg/dL /44b' | Lower-Risk | Intermediate | Higher-Risk |
|---|---|---|---|---|
| Large VLDL /44'<br>(triglyceride) | 110 /44a' | less than 7 | 7-33 | greater than 33 |

LDL Particle concentration categories correspond to NCEP categories for LDL cholesterol (on a percentile equivalence basis), and provide an alternative target for therapy. Large HDL is the protective component of HDL-levels below the 20th percentile indicate higher risk (positive risk factor) and above the 80th percentile lower risk (negative risk factor). Elevations of Large VLDL are related to delayed chylomicron clearance and higher CHD risk-values above the 80th percentile define the "higher-risk" category.

*Goal for secondary prevention (patients with established CHD or diabetes)

FIG. 11

NMR LipoProfile™ Summary Report

| Patient Name | Sex | Age | Physician Name & Address |
|---|---|---|---|
| Patient #5 | | | |

| Patient ID | Birth Date | Specimen ID | |
|---|---|---|---|
| | | LP001141 | Phone: ( ) <br> FAX: ( ) |

| Date Collected | Date Received | Date Reported | Comments |
|---|---|---|---|
| | 04-02-99 | 04-05-99 | |

LIPID PROFILE

Current NCEP Risk Categories

| | mg/dL | Desirable | Borderline-High | High |
|---|---|---|---|---|
| Total Cholesterol | 219 | less than 200 | 200-239 | 240 or greater |

| | mg/dL | Optimal* | Desirable | Borderline-High | High Risk |
|---|---|---|---|---|---|
| LDL Concentration (cholesterol equivalents) | 142 | less than 100* | 100-129 | 130-159 | greater than 160 |

| | mg/dL | Negative Risk Factor | Intermediate | Positive Risk Factor |
|---|---|---|---|---|
| HDL concentration (cholesterol equivalents) | 32 | 60 or greater | 59-35 | less than 35 |

| | mg/dL | Desirable | Borderline-High | High |
|---|---|---|---|---|
| Triglycerides | 330 | less than 200 | 200-400 | 400-1,000 |

Lipid profile values are determined by measuring plasma lipoprotein levels directly by NMR, and converting concentrations to cholesterol or triglyceride units. NMR and standard lipid panel values agree closely for most patients. However, patients with certain metabolic abnormalities or elevated triglycerides may have cholesterol-depleted LDL. NMR LDL concentrations in these cases will be higher than those inferred by standard LDL cholesterol tests, and provide a possibly better indication of CHD risk.

SUBCLASS PROFILE

| | nmol/L | Optimal* | Desirable | Borderline-High | High Risk |
|---|---|---|---|---|---|
| LDL Particle Concentration | 1925 | less than 1100 | 1100-1399 | 1400-1799 | greater than 1800 |

| | nm | Pattern A (large LDL) | Intermediate Size | Pattern B (small LDL) |
|---|---|---|---|---|
| LDL Size | 1925 | 22.0-20.6 | 20.5-20.4 | 20.3-19.0 |
| | | Lower-Risk | | Higher-Risk |

| | nmol/L | Negative Risk Factor | Intermediate | Positive Risk Factor |
|---|---|---|---|---|
| Large HDL (cholesterol) | 11 | greater than 42 | 42-18 | less than 18 |

| | mg/dL | Lower-Risk | Intermediate | Higher-Risk |
|---|---|---|---|---|
| Large VLDL (triglyceride) | 110 | less than 7 | 7-33 | greater than 33 |

LDL Particle Concentration categories correspond to NCEP categories for LDL cholesterol (on a percentile equivalence basis) and provide an alternative target for therapy. Large HDL is the protective component of HDL; values <18 mg/dL (20th percentile) indicate higher risk (positive risk factor) and >42 mg/dL (80th percentile) lower risk (negative risk factor). Large VLDL elevations are related to delayed chylomicron clearance and higher CHD risk; values >33 mg/dL (80th percentile) define the "higher-risk" category.

*Goal for secondary prevention (patients with established CHD or diabetes)

FIG. 11A

NMR LipoProfile™ Technical Report

| Patient Name | Specimen ID | Date Reported |
|---|---|---|
| Patient #5 | LP001141 | 04-05-99 |

CHD RISK ASSESSMENT MODULE

Elevated Number of LDL Particles — Upper 50% ☑
Unlike LDL cholesterol, LDL particle concentration (related closely to plasma apo B level), may be the single best indicator of LDL-associated CHD risk (Lamarche et al., Circulation 1996;94:273-278) and the best target of risk reduction therapy.

Atherogenic Dyslipidemia ☑
Patients with a clustering of the lipoprotein subclass abnormalities listed below are at higher risk of CHD when LDL particle numbers are elevated. Check marks in 2 or more of the boxes below indicate the presence of this higher-risk metabolic condition.

**\* Small LDL** — Pattern B ☑
Small LDL (Pattern B) is a hallmark of "atherogenic dyslipidemia" and confers about three-fold higher risk compared to the large LDL trait (Pattern A). Evidence suggests that small LDL particles may be inherently more atherogenic than large LDL.

**\* Low Level of Large HDL** — Lower 33% ☑
Only the larger HDL subclasses appear to be protective, whereas small HDL is positively associated with CHD (Freedman et al., Arterioscler Thromb Vasc Biol. 1998;18:1046-53). Large HDL, rather than total HDL cholesterol, may thus be a more sensitive risk factor.

**\* Elevated Level of Large VLDL** — Upper 33% ☑
Elevated levels of large, triglyceride-rich VLDL particles have been associated with CAD severity, independently of plasma triglycerides. High concentrations of large VLDL in fasting plasma are a marker for delayed chylomicron clearance (postprandial lipemia).

SUBCLASS LEVELS

Lipoprotein subclass levels (mg/dL) are given in parentheses above each bar. The height of the bar gives the percent of the population* with equal or lower levels.

VLDL Subclasses (mg/dL Triglyceride) | LDL Subclasses (mg/dL Cholesterol) | HDL Subclasses (mg/dL Cholesterol)

| | Large VLDL (V5+V6) | Medium VLDL (V3+V4) | Small VLDL (V1+V2) | IDL | Large LDL (L3) | Medium LDL (L2) | Small LDL (L1) | Large HDL (H3+H4+H5) | Small HDL (H1+H2) |
|---|---|---|---|---|---|---|---|---|---|
| Value | (110) | (163) | (13) | (14) | (23) | (0) | (105) | (11) | (21) |
| Sign | + | + | + | + | + | + | + | − | + |

The plus and minus signs shown above summarize current medical understanding of the relations between lipoprotein subclass levels and heart disease risk. Plus signs signify a positive association with disease (higher levels = higher risk). Larger plus signs signify especially high-risk subclasses. The minus sign signifies a negative association with disease (higher levels = lower risk).

*Population percentile values are from NMR data obtained from analysis of 3,437 subjects in the Framingham Offspring Study.

FIG. 12

NMR LipoProfile™
Technical Report — 100

| Patient Name | Specimen ID | Date Reported |
|---|---|---|
| Patient #5 | LP001141 | 04-05-99 |

CHD RISK ASSESSMENT MODULE — 150'

Elevated Number Particle Conc. — Upper 50% ☑ — LDL particle concentration (related to plasma apo B level) may be the single best indicator of LDL-associated CHD risk (Lamarche et al., Circulation 1996;94:273-278) and the best target of risk reduction therapy. Levels >1400 nmol/L (30th percentile) are "elevated".

Atherogenic Dyslipidemia ☑ — Patients with a clustering of the lipoprotein subclass abnormalities listed below are at higher risk of CHD when LDL particle concentration is elevated. Check marks in 2 or more of the boxes below indicate the presence of this higher-risk metabolic condition.

* Small LDL — Pattern B ☑ — Small LDL (Pattern B) is a hallmark of "atherogenic dyslipidemia" and confers about three-fold higher risk compared to the large LDL trait (Pattern A). Evidence suggests that small LDL particles may be inherently more atherogenic than large LDL.

* Low Level of Large HDL — <23 mg/dL ☑ — Only the larger HDL subclasses appear to be protective, whereas small HDL is positively associated with CHD (Freedman et al., Arterioscler Thromb Vasc Biol. 1998;18:1045-53). Large HDL levels <23 mg/dL (35th percentile) are defined as "low".

* Elevated Level of Large VLDL — >17 mg/dL ☑ — Elevated levels of large VLDL subclasses in fasting plasma are associated with CAD severity independently of plasma triglycerides, and are a marker for delayed chylomicron clearance. Large VLDL levels >17 mg/dL (65th percentile) are defined as "elevated".

SUBCLASS LEVELS

Lipoprotein subclass levels (mg/dL) are given in parentheses above each bar. The height of the bar gives the percent of the population* with equal or lower levels.

| VLDL Subclasses (mg/dL Triglyceride) | | | LDL Subclasses (mg/dL Cholesterol) | | | | HDL Subclasses (mg/dL Cholesterol) | |
|---|---|---|---|---|---|---|---|---|
| Large VLDL (V5+V6) | Medium VLDL (V3+V4) | Small VLDL (V1+V2) | IDL | Large LDL (L3) | Medium LDL (L2) | Small LDL (L1) | Large HDL (H3+H4+H5) | Small HDL (H1+H2) |
| (110) | (163) | (13) | (14) | (23) | (0) | (105) | (11) | (21) |
| + | + | + | + | + | + | + | − | + |

The plus and minus signs shown above summarize current medical understanding of the relations between lipoprotein subclass levels and heart disease risk. Plus signs signify a positive association with disease (higher levels = higher risk). Larger plus signs signify especially high-risk subclasses. The minus sign signifies a negative association with disease (higher levels = lower risk).

*Population percentile values are from NMR data obtained from analysis of 3,437 subjects in the Framingham Offspring Study.

FIG. 12A

NMR LipoProfile DM
Heart Disease Report /—110

| Patient Name | Sex | Age | Physician Name & Address |
|---|---|---|---|
| Patient #5 | | | |

| Patient ID | Birth Date | Specimen ID | Phone: ( ) |
|---|---|---|---|
| | | LP001141 | FAX: ( ) |

| Date Collected | Date Received | Date Received | Comments |
|---|---|---|---|
| | 04-02-99 | 04-05-99 | |

SUBCLASS PROFILE

401 →

| | | Optimal* | Desirable | Borderline-High | High Risk |
|---|---|---|---|---|---|
| LDL Particle Concentration | nmol/L 1925 | less than 1100 | 1100-1399 | 1400-1799 | greater than 1800 |

| | | Pattern A (large LDL) | Intermediate Size | Pattern B (small LDL) |
|---|---|---|---|---|
| LDL Size | nm 19.5 | 22.0-20.8 | 20.5-20.4 | 20.3-19.0 |
| | | Lower-Risk | | Higher-Risk |

| | | Negative Risk Factor | Intermediate | Positive Risk Factor |
|---|---|---|---|---|
| Large HDL (cholesterol) | mg/dL 11 | greater than 42 | 42-18 | less than 18 |

| | | Lower-Risk | Intermediate | Higher-Risk |
|---|---|---|---|---|
| Large VLDL (triglyceride) | mg/dL 110 | less than 7 | 7-33 | greater than 33 |

LDL Particle Concentration categories correspond to NCEP categories for LDL cholesterol (on a percentile equivalence basis) and provide an alternative target for therapy. Large HDL is the protective component of HDL; values <18 mg/dL (20th percentile) indicate higher risk (positive risk factor) and >42 mg/dL (80th percentile) lower risk (negative risk factor). Large VLDL elevations are related to delayed chylomicron clearance and higher CHD risk; values >33 mg/dL (80th percentile) define the "higher-risk" category.

*Goal for secondary prevention (patients with established CHD or diabetes)

150' — CHD RISK ASSESSMENT MODULE

151 — Elevated LDL Particle Conc. >1400 nmol/L ☑ — LDL particle concentration (related to plasma apo B level) may be the single best indicator of LDL-associated CHD risk (Lamarche et al., Circulation 1996;94:273-278) and the best target of risk reduction therapy. Levels >1400 nmol/L (50th percentile) are "elevated".

152 — Atherogenic Dyslipidemia ☑ — Patients with a clustering of the lipoprotein subclass abnormalities listed below are at higher risk of CHD when LDL particle concentration is elevated. Check marks in 2 or more of the boxes below indicate the presence of this higher-risk metabolic condition.

* Small LDL /—153 Pattern B ☑ — Small LDL (Pattern B) is a hallmark of "atherogenic dyslipidemia" and confers about three-fold higher risk compared to the large LDL trait (Pattern A). Evidence suggests that small LDL particles may be inherently more atherogenic than large LDL.

* Low Level of Large HDL /—154 <23 mg/dL ☑ — Only the larger HDL subclasses appear to be protective, whereas small HDL is positively associated with CHD (Freedman et al., Arterioscler Thromb Vasc Biol. 1998;18:1046-53). Large HDL levels <23 mg/dL (35th percentile) are defined as "low".

* Elevated Level of Large VLDL /—155 >17 mg/dL ☑ — Elevated levels of large VLDL subclasses in fasting plasma are associated with CAD severity independently of plasma triglycerides, and are a marker for delayed chylomicron clearance. Large VLDL levels >17 mg/dL (65th percentile) are defined as "elevated".

FIG. 13

Image# METHODS, SYSTEMS, AND COMPUTER PROGRAM PRODUCTS FOR ANALYZING AND PRESENTING NMR LIPOPROTEIN-BASED RISK ASSESSMENT RESULTS

RELATED APPLICATIONS

This application is a divisional of U.S. application Ser. No. 09/291,736 filed Apr. 14, 1999, now abandoned which is a continuation in part of U.S. application Ser. No. 09/258,740 filed Feb. 26, 1999. The contents of these applications are hereby incorporated by reference as if recited in full herein.

FIELD OF THE INVENTION

The present invention relates generally to analysing and reporting patient specific medical information.

BACKGROUND OF THE INVENTION

Recently, a significant advance in measurement techniques used to analyze blood plasma lipoprotein samples was achieved. Lipoproteins are the spherical particles that transport cholesterol, triglycerides, and other lipids in the bloodstream. The advanced measurement technique employs NMR spectroscopy to provide additional (higher-order) patient-specific information over the types of information typically provided under routine conventional analysis methods. See U.S. Pat. No. 4,933,844 to Otvos, entitled "Measurement of Blood Lipoprotein Constituents by Analysis of Data Acquired From an NMR Spectrometer" and U.S. Pat. No. 5,343,389 to Otvos, entitled "Method and Apparatus for Measuring Classes and Subclasses of Lipoproteins." The contents of these documents are hereby incorporated by reference as if recited in full herein. Unlike conventional "routine" laboratory lipoprotein blood tests, the lipoprotein analysis provided by the NMR spectral analysis now more easily provides lipoprotein subclass information, which had, until this advance, been generally inaccessible to clinicians. This subclass information can provide information corresponding to the sizes of the lipoprotein particles that make up a person's lipoprotein constituents.

Lipoprotein subclass information is not included in conventional commercially prepared lipid panels. The conventional panels typically only provided information concerning total cholesterol, triglycerides, low-density lipoprotein (LDL) cholesterol (generally a calculated value), and high-density lipoprotein (HDL) cholesterol. In contrast, the NMR analysis can provide information about (a) the concentrations of six subclasses of very low density lipoprotein (VLDL), four subclasses of LDL (including intermediate-density IDL), and five subclasses of HDL, (b) average LDL particle size (which can be used to categorize individuals into LDL subclass pattern-determined risk), and (c) LDL particle concentration.

The subclass information now available with the NMR spectral analysis can be a more reliable indicator of a patient's risk to develop coronary heart disease. Indeed, recent scientific research has shown that various subclasses of lipoproteins may provide more reliable markers of the metabolic conditions that predispose individuals to a greater or lesser risk of heart disease. However, the NMR spectral analysis can also provide higher-order information about the levels of variously atherogenic or antiatherogenic subclasses that make up each of the major lipoprotein classes.

This subclass information can provide a clear indication about a patient's propensity to develop coronary heart disease. Unfortunately, this additional information can confuse a reviewer as to the meaning of the data, and further, the additional information can be difficult to analyze in a readily discernable manner. For example, a typical NMR lipoprotein analysis can include at least fifteen more values of lipoprotein concentration and size than is provided by standard lipoprotein panels. There is, therefore, a need to analyze and present the lipoprotein-based information in a manner or format which is visually easy to read and understand and which provides a useful coronary heart disease risk assessment.

OBJECTS AND SUMMARY OF THE INVENTION

It is therefore an object of the present invention to provide a method to analyze patient-specific NMR based lipoprotein measurements in a manner which yields a reliable indicator of an associated risk of developing coronary heart disease.

It is an additional object of the present invention to provide a lipoprotein profile analysis with subclass information with an easily read display format.

It is also an object of the present invention to provide a lipoprotein-based risk assessment which analyzes a patient's measured major lipoprotein constituent values and/or selected subclass information and presents them in a format in which a patient's specific values are presented in a reader-friendly format.

It is a further object of the present invention to provide a method of generating a customized report at a commercial volume and which can analyze and/or report a patient's risk factors for coronary heart disease based on NMR-based measurements of lipoprotein constituents.

It is still another object of the invention to alert the patient or physician of a reduced lipoprotein constituent value for a secondary prevention goal for patients with underlying metabolic disorders.

It is an additional object of the present invention to provide a system for measuring lipoprotein constituents and analyzing the constituent values in a manner which determines CHD risk.

These and other objects of the present invention are provided by a method for identifying a patient with an increased risk of coronary heart disease by analyzing the patient's NMR lipoprotein constituent measurements. This analysis includes determining a risk for a specific constituent identified as having an independently predictive factor (in isolation of the other constituent values) and for a combination of certain of the constituent measurement values. Preferably, the combination method identifies whether the patient's results provide a positive match with two key NMR measured lipoprotein factors. The first factor is the determination of the presence of atherogenic dyslipidemia (i.e., a clustering of predetermined level moderate, borderline, or positive NMR subclass or constituent based risk values) and the second factor is the detection of an elevated number of NMR measured LDL particles. Advantageously, this type of risk analysis is typically more accurate than the plasma apo B level techniques used in the past, and can provide a more reliable indictor as it more closely corresponds to a patient's true lipoprotein composition.

In particular, a first aspect of the present invention is directed to a method for assessing a patient's risk of coronary heart disease based on personalized NMR measured lipoprotein-based information. The method includes generating NMR-based lipoprotein measurement values for a patient's blood plasma or serum sample, the NMR-based lipoprotein measurement values comprising a plurality of lipoprotein constituent values including a constituent value for LDL particle concentration. The LDL particle concentration is compared with predetermined test criteria for determining whether the LDL particle concentration is elevated and a plurality of NMR-based lipoprotein constituent values are compared to predetermined test criteria to determine the presence of atherogenic dyslipidemia. A patient's risk of coronary heart disease is assessed based on one or more of the LDL particle elevated concentration level and the presence (or absence) of atherogenic dyslipidemia.

In a preferred embodiment, the NMR-based lipoprotein constituent values include the major lipoprotein constituents of total cholesterol, LDL concentration in cholesterol equivalents, HDL concentration in cholesterol equivalents, and triglycerides, and the measured lipoprotein constituent values also include the values associated with LDL size, LDL particles, large HDL cholesterol, and large VLDL triglyceride. It is also preferred that the NMR based lipoprotein constituent values used to determine the presence of atherogenic dyslipidemia is independent to the LDL particle concentration value (i.e., does not include the isolated LDL particle concentration value as part of the subtest criteria for determining atherogenic dyslipidemia). Preferably, the predetermined test criteria for determining the presence of an elevated number of LDL particles is set at a value which is in about the upper 50% of the population (at least moderately elevated). Of course, the presence of atherogenic dyslipidemia when an elevated LDL particle concentration also exists is particularly indicative of the presence of a higher-risk metabolic condition.

Another aspect of the present invention is directed to a method of presenting NMR derived lipoprotein subclass information in a two-dimensional window. The method includes obtaining a plurality of lipoprotein constituent values associated with NMR based lipoprotein measurements including the values associated with LDL size, LDL particles, large HDL cholesterol, and large VLDL triglyceride and identifying a risk level associated with coronary heart disease for each of the obtained NMR based lipoprotein constituent values. The obtained lipoprotein constituent values are then analyzed to determine the associated risk level and the obtained lipoprotein constituent values are arranged in a display format which positions the lipoprotein constituent values adjacent to a corresponding risk analysis portion, wherein the risk analysis portion has a plurality of discrete segments characterizing the constituent value's determined risk level. The discrete risk segment corresponding to the actual constituent value within the respective risk analysis portion is visually enhanced such that the risk associated with the lipoprotein constituent value is readily apparent. Preferably, the obtaining step also obtains the NMR based lipoprotein constituent values for the major lipoprotein constituents of total cholesterol, LDL concentration in cholesterol equivalents, HDL concentration in cholesterol equivalents, and triglycerides. It is also preferred that the risk analysis for LDL concentration in cholesterol equivalents and the LDL particle concentration includes four discrete risk segments (corresponding to optimal, desirable, borderline-high, and high risk) and wherein each of the discrete risk segments corresponds to a predetermined level associated with its occurrence in the general population. Preferably, the remainder of the lipoprotein constituent values risk analysis segments are configured with three discrete segments, and the risk analysis discrete segments for the non-major lipoprotein constituent values are configured to mirror the risk level defined for the risk analysis discrete segments for the major lipoprotein constituents. (Typically, the risk analysis segment defines the risk level such that it corresponds to the occurrence of the value as defined by a population percentile).

In a preferred embodiment, the optimal value is a reduced target value for secondary prevention.

Another aspect of the present invention is an automatically produced lipoprotein report including data corresponding to NMR-derived measurements. The report comprises a first lipid profile segment comprising a plurality of NMR derived major lipoprotein constituent values, wherein each major lipoprotein value has an associated risk analysis portion and a second subclass profile segment comprising a plurality of NMR derived subclass variables, each subclass variable having an associated risk analysis portion which is configured to visually enhance the risk of developing coronary heart disease for each of the plurality of subclass variable information. The lipoprotein report is generated at a commercial scale at automatically generated by a computer based on NMR derived patient-specific information. Further, at least the subclass profile segment includes a reduced target value associated with at least one subclass value associated with a goal of secondary prevention, thereby facilitating the awareness of the existence of an underlying metabolic disorder and providing a visual reminder to pursue a more aggressive reduction of at least one lipoprotein value compared to the general population.

In a preferred embodiment, the reduced target value is identified as an optimal risk category for both the LDL concentration in cholesterol equivalents and the LDL particle concentration in the risk analysis portions. It is also preferred that the report include a coronary heart disease risk assessment module. The risk assessment module provides additional information about coronary heart disease risks associated with an elevated number of LDL particles and the determination of the presence of atherogenic dyslipidemia associated with a clustering of selected abnormal subclass values.

Still another aspect of the invention is an automatically produced lipoprotein report which is generated at a commercial laboratory based on data corresponding to NMR-derived measurements. The automated report comprises a subclass profile segment comprising a plurality of patient-specific NMR derived lipoprotein constituent values, each constituent value having an adjacently positioned associated risk analysis portion which visually identifies the value with one of at least three discrete risk categories corresponding to a coronary heart disease risk level associated with the NMR-derived measurement value. Preferably, the automatically produced lipoprotein report includes LDL particle concentration as one of the NMR derived lipoprotein constituent values and the corresponding risk analysis portion includes four risk categories: one associated with a desirable concentration level; one associated with a borderline-high level; one associated with an increased or higher risk level; and one associated with an optimal level corresponding to a goal for secondary prevention.

An additional aspect of the present invention is a computer program product for personalized lipoprotein-based risk assessment. The computer program product comprises a computer readable storage medium having computer readable program code means embodied in the medium. The computer-readable program code means comprising a computer readable program code means for generating NMR-based lipoprotein measurement values for a patient's blood sample, the lipoprotein measurement values including at least one subclass variable value. The computer program product also includes a computer readable program code means for comparing the at least one patient lipoprotein subclass variable value with predetermined test criteria for determining whether the at least one subclass variable value is associated with a higher or lower risk of developing coronary heart disease and computer readable program code means for identifying, for the at least one measured subclass variable value, the corresponding risk level associated with coronary heart disease. The computer program product also includes a computer readable program code means for providing a risk analysis portion adjacent to the measured lipoprotein values, the risk analysis portion displaying information corresponding to higher and lower coronary heart disease risk. The measured value is visually enhanced in the risk analysis portion to visibly indicate the level of risk associated therewith to thereby provide a contemporaneous reference guideline for interpretation of the measured value. The computer program product additionally includes a computer readable program code means for comparing a plurality of the NMR-based lipoprotein measurement values to predetermined test criteria to determine the presence of atherogenic dyslipidemia.

In a preferred embodiment, the NMR-based lipoprotein values include the major lipoprotein constituents of total cholesterol, LDL concentration in cholesterol equivalents, HDL concentration in cholesterol equivalents, and triglycerides, and the subclass values associated with LDL size, LDL particles, large HDL cholesterol, and large VLDL triglyceride, and the computer program product further comprises computer readable program code means for presenting the lipoprotein measurement values such that each of the lipoprotein measurement values is substantially aligned. It is also preferred that the risk analysis portion for each of LDL concentration in cholesterol equivalents and LDL particles is divided into four risk categories, and that the remainder of the risk analysis portions is divided into three discrete segment risk categories.

Preferably, for the reports, methods, and computer program products directed to lipoprotein information, the measured lipoprotein values include (a) the major lipoprotein constituents of total cholesterol, LDL concentration in cholesterol equivalents, HDL concentration in cholesterol equivalents, and triglycerides and (b) the LDL size and the concentration level of LDL particles, large HDL cholesterol, and large VLDL triglyceride.

The present invention is advantageous because it provides NMR-derived lipoprotein results with associated risk information in a format that is easy to understand and aesthetically pleasing. Further, the patient's specific subclass profile is presented in the risk assessment report in a graphically enhanced or visually emphasized format so the clinician or layman can easily understand the risk category associated with one or more of a patient's subclass values. Further, the customized report is provided in a computer program product allowing mass or commercial level automated production of a summary report which includes a risk analysis portion which can be customized to report the patient's results in a visually enhanced format. Advantageously, the report or risk assessment method flags or alerts the treating physician or patient as to the reduced target goal for LDL concentration and LDL particle concentration for patients with underlying metabolic disorders such as established or previously diagnosed coronary heart disease, diabetes, or other vascular disorders. This secondary prevention goal is preferably visibly presented to alert and facilitate the ongoing counseling for such a patient to reinforce the importance of behavioral modifications or other therapy.

BRIEF DESCRIPTION OF THE DRAWINGS

FIG. 1 illustrates a lipoprotein summary report according to the present invention.

FIG. 2 illustrates a risk assessment report according to one embodiment of the present invention which may be included in or provided separate from the lipoprotein summary report of FIG. 1.

FIG. 2A illustrates an alternative embodiment of the risk report shown in FIG. 2.

FIG. 5 illustrates a supplemental risk factor segment of the risk assessment report of FIG. 2.

FIG. 7 illustrates a primary prevention risk assessment segment of the risk assessment portion of FIG. 2.

FIG. 7A illustrates a prevention risk assessment segment having positive risk factors identified as negative numbers to be added to negative risk factors having positive numbers such as those shown in FIG. 7 to provide an overall adjusted risk assessment according to the present invention.

FIG. 8 illustrates a secondary risk segment including information regarding high-risk medical conditions for the risk assessment report of FIG. 2A.

FIG. 11 illustrates an alternate embodiment of a coronary heart disease analysis or lipoprotein measurement report.

FIG. 11A illustrates the report of FIG. 11 with a modified subclass profile providing values associated with defined risk factors.

FIG. 12 illustrates a risk assessment module identifying the presence of atherogenic dyslipidemia according to a preferred embodiment of the present invention.

FIG. 12A illustrates an alternate embodiment of a risk assessment module according to the present invention.

FIG. 13 illustrates yet another embodiment of a report according to the present invention.

DETAILED DESCRIPTION OF THE INVENTION

Figure 3:
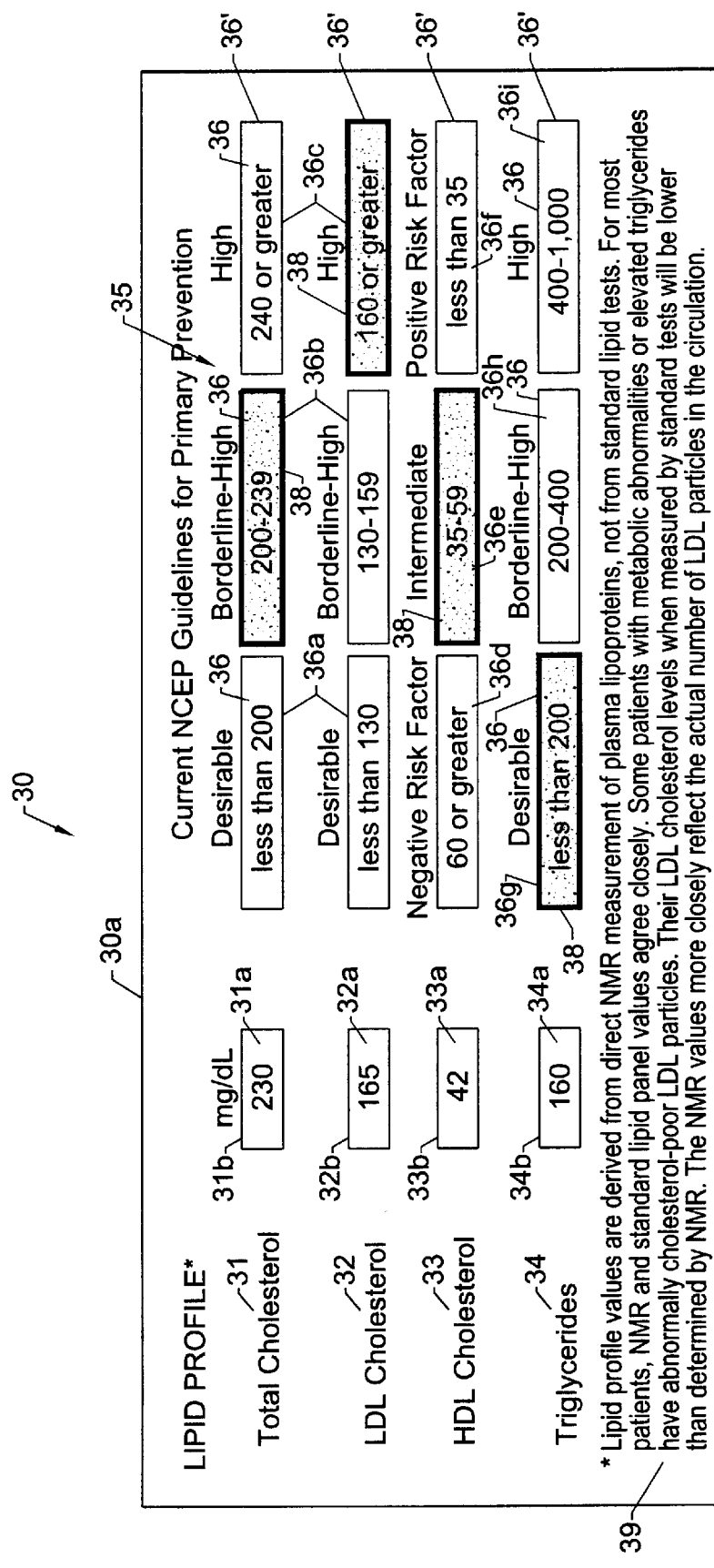
FIG. 3 illustrates a lipid profile segment of the lipoprotein summary report of FIG. 1.

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Referring now to FIG. 1, a preferred embodiment of a NMR lipoprotein profile summary report 10 is shown. Preferably, the lipoprotein profile summary report 10 is divided into at least three horizontally oriented segments 20, 30, 40. The first segment 20 of the summary report 10 includes patient identification data 21 such as a name, identification number, and any relevant personal history such as age, smoking status, and other related medical history. As shown, the first segment 20 can also include physician data 22 and a comment section 23. The second segment 30 of the summary report 10 presents the lipid profile analysis and will be discussed further below. The third segment 40 of the summary report 10 presents the subclass profile analysis and will also be discussed further below.

As shown in FIG. 2, the summary report 10 can also include a risk assessment report 10' containing information targeted to a more detailed risk assessment. Of course, the summary report 10 and the risk assessment report 10' as well as individual segments of each can be individually reported, presented or provided. In any event, as shown, the risk assessment report 10' includes a fourth segment 50 which presents supplemental risk factors, and a fifth segment 60 containing individual lipoprotein subclass levels. The summary report 10 can also include an optional sixth segment 70 which can incorporate primary prevention risk assessment information which can predict long term (i.e., 10 year) coronary heart disease (CHD) risk percentages.

As shown in FIG. 2A, a risk assessment report 10" can also include a seventh segment 80 directed to secondary prevention guidelines which can summarize high risk conditions and characterizations, such as atherosclerotic vascular disease and diabetes, and general lipid management goals. This secondary prevention information may help to assist medical personnel in alternative treatment and to alert as to potential high-risk behavior or conditions. As shown, the risk assessment report is rearranged to present the fourth segment 50, the sixth segment 60, and the seventh segment 80. The information in this sample risk assessment report 10" is from a different patient than the results shown in FIGS. 1 and 2.

In a preferred embodiment, the major lipoprotein constituent values and the selected subclass values are generated via the NMR spectral analysis discussed above. The data are typically obtained by processing a blood plasma or serum sample obtained from a subject. As such, as used herein the terms "blood" and "plasma and "serum" sample are interchangeable, as each is suitable for obtaining the desired NMR spectroscopy signal.

Turning now to FIG. 3, a preferred embodiment of the lipid profile or second segment 30 of the summary report 10 is shown. The patient-specific lipid value results of total cholesterol 31, LDL cholesterol 32, HDL cholesterol 33, and triglycerides 34 are listed and arranged in aligned order from a top portion 30a of the second segment to a bottom portion 30b of the second segment. Preferably, alongside the listed order of the total cholesterol, LDL, HDL, and triglycerides, 31, 32, 33, and 34, respectively, the associated actual measured values 31a, 32a, 33a, and 34a are also serially aligned. Preferably, the values 31a, 32a, 33a, 34a are each displayed in a box 31b, 32b, 33b, 34b. Of course, the values 31a, 32a, 33a, and 34a may otherwise be presented, but are preferably presented in a visually enhanced format (such as via bold, italics, shaded, font (size, type), circled, underlined, colored or highlighted by other visual enhancement means) to provide ready visual recognition of the patient-specific results.

As is also shown in FIG. 3, the second segment 30 also preferably includes risk assessment guidelines 35 which represent a relative reference, guideline, or "yardstick" of the patient's value as compared to targeted values. Preferably, the risk assessment guidelines 35 divide the respective measured patient value for each of the total cholesterol 31, LDL 32, HDL 33, and triglycerides 34 into three different categories 36 of risk associated with a predetermine range of values (shown as measured in mg/dL). These predetermined range of values are based on predetermined test criteria.

As shown, the three categories for total cholesterol 31 and LDL 32 are labeled desirable 36a, borderline-high 36b, and high 36c. As shown, for total cholesterol 31, the desirable 36a category is defined as a value less than 200. For LDL 32, the desirable category 36a, is defined as a value less than 130. The borderline-high category 36b is defined as a range of values between 200–239 for total cholesterol 31 and between 130–159 for LDL 32. The high category 36c is defined as 240 or greater for total cholesterol 31 and 160 or greater for LDL 32.

Referring again to FIG. 3, the HDL categories 36 are labeled as negative risk factor 36d, intermediate 36e, and positive risk factor 36f The negative risk factor 36d is defined as a value of 60 or greater, the intermediate risk category 36e is defined as a value between and including 35–59, and the positive risk factor 36f is defined as a value less than 35.

The triglycerides categories 36 are labeled as normal 36g, borderline-high 36h, and high 36i. The normal category 36g is defined as a triglyderides value 33 of less than 200, the borderline-high category 36h is defined as a value between 200–400, and the high category 36i is defined as a value greater than 400 (but typically below 1000).

Preferably, the predetermined test criteria or targeted or ranges of values associated with each category of risk 36a–36i are defined to correspond to current National Cholesterol Education Program (NCEP) guidelines for primary prevention of coronary heart disease. See National Cholesterol Education Program, *Second Report of the Expert Panel on Detection, Evaluation, and Treatment of High Blood Cholesterol in Adults (Adult Treatment Panel II)*, Circulation 1994; 89:1329–1445. Of course, other suitable values or definitions can also be used, such as population based norms or other targeted based norms.

Preferably, as shown in FIGS. 1 and 3, the risk category 36 which corresponds to the patient value is visibly enhanced so that a reader can readily discern the category associated with the patient specific result (ie., a visually enhanced risk category 38). For example, a person reviewing the patient-specific results shown in FIG. 3 can readily discern that the patient results indicate that the patient is "high risk" in one category (LDL cholesterol 32), intermediate/borderline in two categories (cholesterol 31 and HDL cholesterol 33), and desirable in the other category (triglycerides 34). Further, a reviewer could readily discern how close the measured value is to the next adjacent risk category for each value 31, 32, 33, 34, which can also facilitate a more complete understanding of the results.

Preferably, as shown, the risk assessment 35 is formatted so that the three risk categories 36 for each measured value are similarly sized and configured and are arranged serially over or under the adjacent measured value. In this way, each of the categories 36 for each measured value is positionally vertically aligned. The "low" or "negative/good" risk values 36a, 36d, 36g are positioned on one edge of a risk bar 36' and the "high" or "bad/positive" risk values 36c, 36f, 36i are positioned at the opposing edge of the risk bar 36'. This presentation yields an aesthetic, easily readable format and informational horizontal continuum of risk characterization associated with the patient's results. As is also shown, the summary report 10 (or one or more of the segments 20, 30, 40) can include a descriptive comment portion 39 which discusses slight differences which may be observed from NMR spectral measurements compared to conventional or standard tests.

Figure 4:
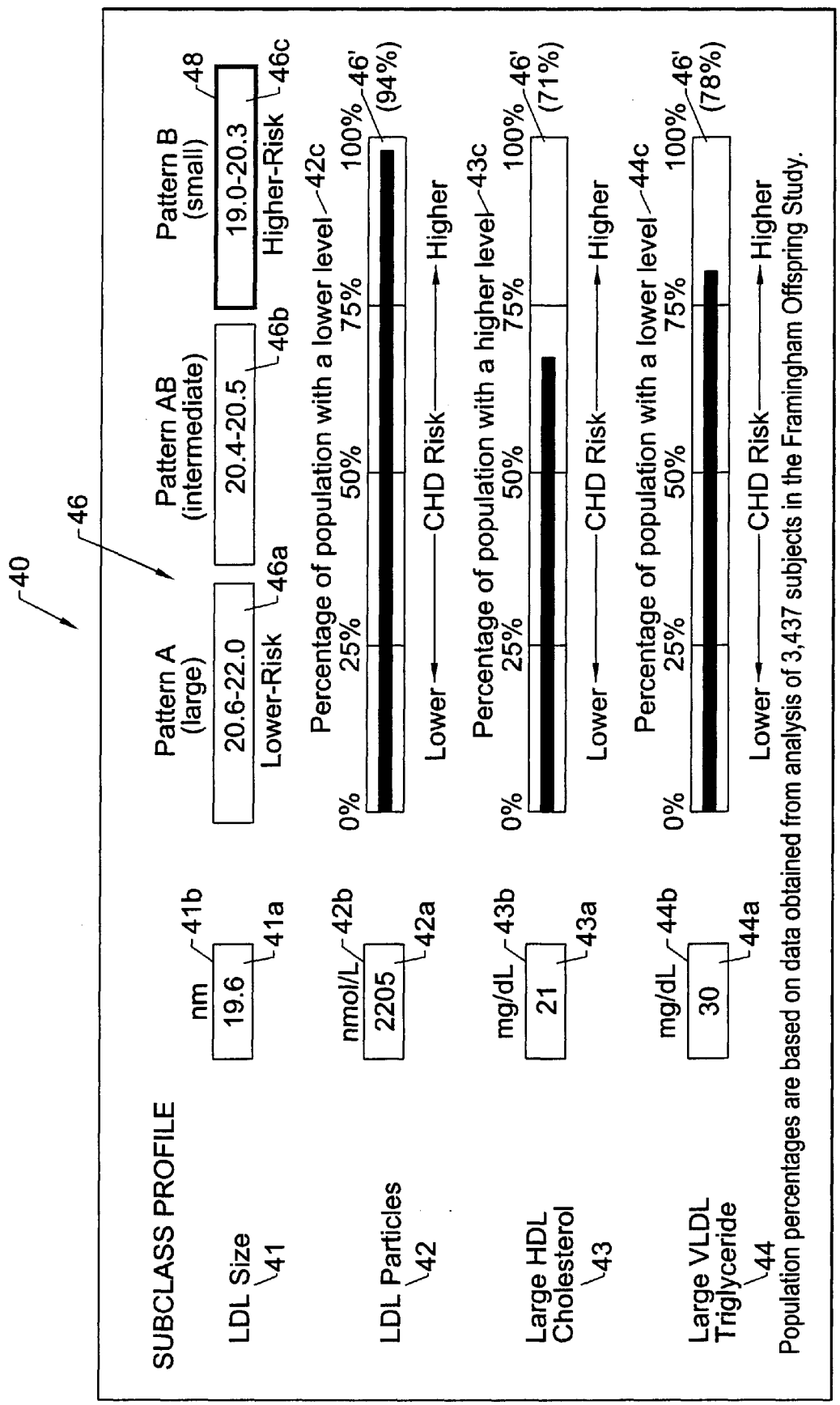
FIG. 4 illustrates a subclass profile segment of the lipoprotein summary report of FIG. 1.

Turning now to FIG. 4, a preferred embodiment of the third segment 40 of the summary report 10 presenting the subclass profile is shown. The third segment 40 preferably includes four measured subclass variables, the subclass variables being labeled as LDL size 41, LDL particles 42, large HDL cholesterol 43, and large VLDL triglyceride 44. The LDL size value 41a is shown as measured in nanometers (nm). The LDL particles value 42a is shown as measured in nanomoles per liter (nmol/L) while the large HDL cholesterol value 43a and the large VLDL triglyceride value 44a are measured in milligrams per deciliter (mg/dL).

As for the lipid profile results discussed for the second segment 30 above, each of the measured values 41a, 42a, 43a, 44a are preferably presented in a visually enhanced manner 41b, 42b, 43b, 44b (the results are shown as visually enhanced or offset by a frame or box).

In a preferred embodiment, the third segment 40 also includes a risk assessment portion 46 where the measured results 41a, 42a, 43a, and 44a are visually enhanced and related or compared to predetermined criteria or values. For example, the LDL size result 41a is associated with three risk categories 46a, 46b, 46c. The risk categories 46a, 46b, 46c are defined by a pattern (A, AB, or B, respectively) associated with the particle size. The first category 46a is Pattern A, which is defined as a lower risk pattern associated with large particle sizes of 20.6–22.0 nm. The second category 46b is Pattern AB which is defined as an intermediate risk and corresponds to a particle size of 20.4–20.5 nm. The third risk category 46c is Pattern B and is defined as a higher-risk category and corresponds to smaller particle sizes of between 19.0–20.3 nm.

As shown, the remaining subclass measured values 42a, 43a, 44a, are displayed on a horizontally oriented line graph 46'. Preferably, each line graph 46' plots the patient's results to illustrate whether the result indicates a higher or lower risk of CHD. In the embodiment shown, the graph is used to compare the patient measured result against a percentage of the general population having higher or lower levels of the measured value. Preferably, as shown, the line graphs 46' are plotted such that the results show a greater risk aligned at the right edge of the graph 46'. Stated differently, whether a higher or lower value indicates a higher risk of CHD, each of the line graphs 46' are defined to present the measured value such that the higher risk of CHD is at the same edge of the line graph and the higher and lower risks are thus visually aligned.

For example, the LDL particles 42a and the large VLDL triglyceride values 44a are graphed corresponding to percentage of the population having lower values 42c, 44c while the large HDL value 43a is graphed corresponding to the percentage of population having a higher value 43c. Nonetheless, as shown, the line graphs 46' are oriented and plotted such that the higher risk of CHD is aligned along the right end portion of the line graph. As shown, the patient results illustrate that 94% of the population has a lower LDL particle value 42a, 71% of the population has a higher large HDL value 43a, and 78% of the population has a lower large VLDL trigylceride 44a level.

In a preferred embodiment, the population values are based on scientific results obtained from subjects in the Framingham Offspring Study. See Wilson et al., *Impact of National Guidelines for Cholesterol Risk Factor Screening. The Framingham Offspring Study*, JAMA, 1989; 262: 41–44. Of course the values presently defined for the risk assessment 36, 46 portion of the summary may change over time and more or alternate risk categories may be added. Further, the actual ranges or definitions associated with the risk category values of one or more of the lipid panels or subclass categories may change over time and the present invention is not intended to be limited thereto.

The order of the measured values 31a, 32a, 33a, 34a, 41a, 42a, 43a, and 44a may be alternately arranged in the summary report 10. In addition, the layout of the results may be alternately oriented (such as in vertical segments). Of course, the second segment 30 (lipid profile) or the third segment 40 (subclass profile) may be provided alone depending on a customer's specifications.

It is also preferred that the report include a discussion of "flagged" or potential increased risk factors identified by the subclass values 41a, 42a, 43a, 44a as compared to predetermined risk assessment criteria. For example, as shown in FIG. 5, a supplemental risk factor segment 50 can be included in the summary report 10'. The supplemental segment can include a preliminary informational introduction 50a which notes that coronary heart disease risk can significantly increase when there is a clustering of metabolic abnormalities not detected by standard lipid measurements. The supplemental risk segment 50 summarizes the presence of a metabolic profile associated with a higher level of risk than indicated by the LDL cholesterol value 32a. In a preferred embodiment, the "clustering" is indicated by a mark 51a, 52a, 53a, 54a in a corresponding subclass box 51b, 52b, 53b, 54b.

As shown, this supplemental risk factor segment 50 includes a summary 50' for subclass values indicating abnormalities which indicate increased risk, i.e., Pattern B small LDL 51, elevated number of LDL particles 52, low level of large HDL 53, and elevated level of large VLDL 54. As shown, if the summary 50' is selected (shown as positive with a "check mark" proximate to the category), then the CHD risk is increased. An informational guideline 51c, 52c, 53c, 54c, for the abnormal values is positioned proximate to the subclass box.

In an alternative embodiment (not shown), a computer program can be configured to provide the analysis and risk assessment in a manner in which it can suppress non-abnormal results and provide only abnormal results in this segment 50'. Thus, if a patient has two "abnormal" or elevated risk values associated with the subclass readings, then only those two subclasses will be printed on this segment 50 of the summary report 10.

In any event, as indicated for the small LDL variable 51, small LDL size (Pattern B) is a hallmark of the "atherogenic lipoprotein phenotype" and confers approximately a three-fold higher risk compared to the large LDL trait (Pattern A). There is evidence that suggests that small LDL particles may be inherently more atherogenic than large LDL. As regards an elevated number of LDL particles 52 (shown as for a value corresponding to the upper 33% of the population), unlike LDL cholesterol, LDL particle concentration (related closely to plasma apo B level), may be the single best indicator of LDL-associated CHD risk and the best target of risk reduction therapy. See Lamarche et al., Circulation 1996; 94:273–278. The supplemental risk factor segment 50 can also indicate the presence of low levels of large HDL 43. Low levels of large HDL 43 (shown as a value corresponding to the lower 33% of the population) may be a positive risk factor, as only larger HDL subclass particles appear to protect against CHD—whereas small HDL may even be atherogenic. Therefore, large HDL, rather than total HDL cholesterol, may be a more sensitive risk factor. See Freedman et al., Arterioscler. Thromb. Vasc. Biol. 1998; 18:1046–53. Similarly, as shown, elevated levels of large triglyceride rich VLDL particles 54, appear to be associated with coronary artery disease (CAD) severity, substantially independent of plasma triglycerides. High concentrations of large VLDL in fasting plasma may be a marker for delayed chylomicron clearance (postprandial lipemia).

Figure 6:
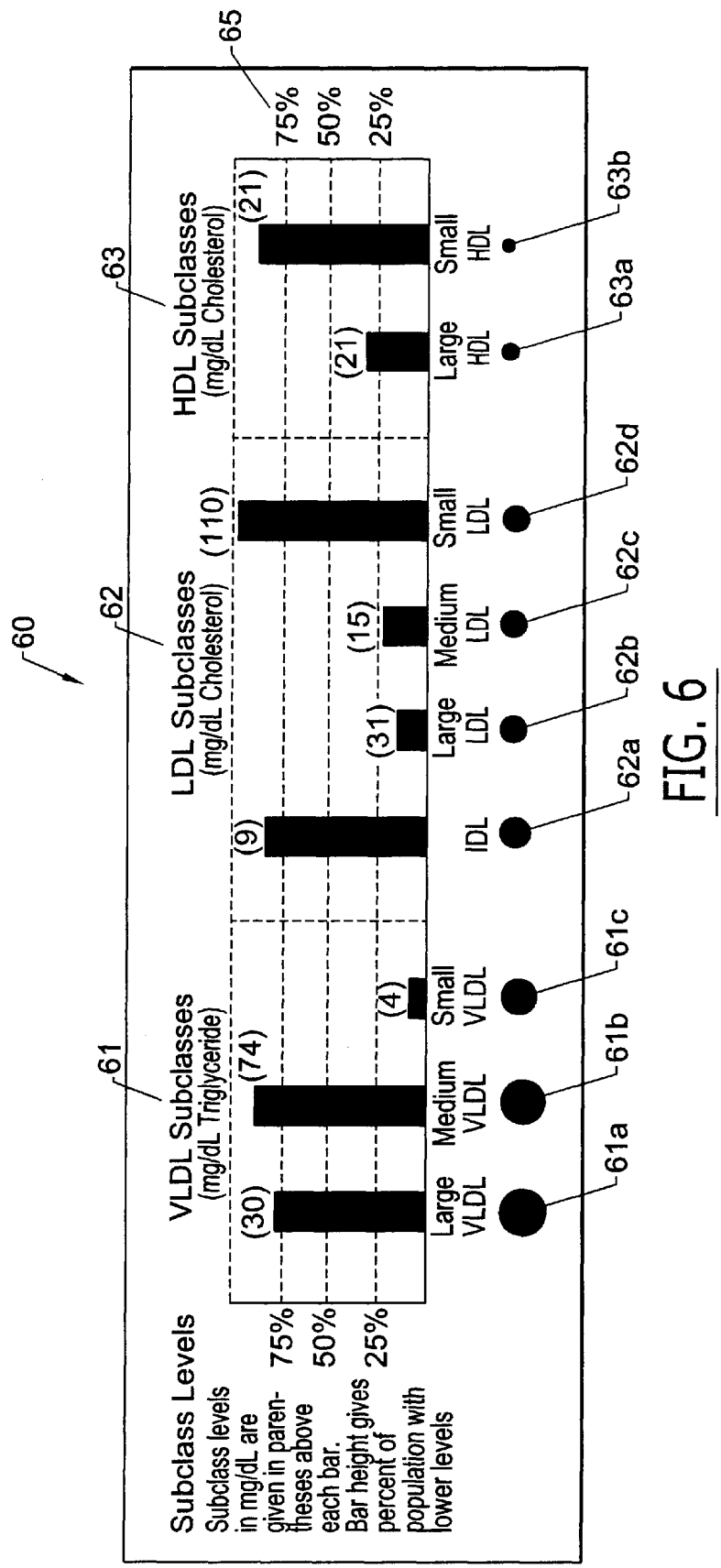
FIG. 6 illustrates a subclass level risk assessment segment for the risk assessment report of FIG. 2.

As shown in FIGS. 2 and 6, the summary report 10 may also include a fifth segment 60 showing a graphical representation of the subclass levels provided by NMR analysis. Referring to FIG. 6, the segment 60 divides the information into three groups of subclasses, VLDL triglyceride subclasses 61, LDL cholesterol subclasses 62, and HDL cholesterol subclasses 63. Each of the three subclasses 61, 62, 63 are further divided to graphically portray selected or grouped results. As shown, the VLDL triglyceride subclass 61 is divided into three groupings, a large VLDL subclass 61*a* (shown with a concentration or value of 30), a medium VLDL subclass 61*b* (shown with a value of 74), and a small VLDL subclass 61*c* (shown with a value of 4). The LDL subclasses 62 shown in FIG. 6 include an IDL cholesterol subclass 62*a* (shown with a value of 9), a large LDL cholesterol subclass 62*b* (shown with a value of 31), a medium LDL cholesterol subclass 62*c* (shown with a value of 15), and a small LDL cholesterol subclass 62*d* (shown with a value of 110). The HDL subclasses shown are large HDL cholesterol 63*a* (shown with a value of 21) and small HDL 63*b* (shown with a value of 21 For each subclass level shown 61*a–c*, 62*a–d*, 63*a–b*, the level measured in mg/dL are provided in text form at the top of the respective bar. The height of the bar gives the percent of population with lower levels of the graphed value. Advantageously, the HDL cholesterol subclass grouping can visually indicate the breakdown of the constituents of the overall HDL class 33 (value 42) shown on the summary report 10 to indicate the correspondence between the two subclasses to the overall HDL number. As shown, the results indicate an even amount of small HDL cholesterol 63*b* versus large HDL cholesterol 63*a*. Of course, other groupings or different subclass information may be separated out such as the separable subclass information shown in FIG. 9, as will be discussed further below.

The risk assessment report 10' may also include a sixth segment 70 addressing the primary prevention risk assessment for an individual. Referring to FIG. 7, the sixth segment 70 incorporates certain behavioral and medical background of an individual with the lipid profile and subclass values. For example, a patient's age, smoking history, blood pressure, LDL value 32 and HDL value 33, and whether he or she has diabetes, and/or other risk pertinent information such as whether a blood relative has diabetes or CHD. A risk factor value is assigned to each of these parameters. Additionally, positive risk factors can be assigned a negative risk value (FIG. 7A). Examples of positive risk factors include whether the patient actively exercises at least three days per week, has a high HDL cholesterol level 33*a*, has a Pattern A LDL size 41*a*, and has elevated levels of large HDL 43*a*). The positive and negative risk factors can be added to yield an overall risk value. In any event, a percentage based predictive CHD risk is generated corresponding to the total calculated risk. A target norm for the patient's age and gender can also be provided.

In a preferred embodiment, the relative "negative" risk factors and predictive analysis is generated as described by Wilson et al., in *Prediction of Coronary Heart Disease Using Risk Factor Categories*, May 12, 1998 (copyright 1998 American Heart Association, Inc.).

As also shown in FIG. 7, the risk of coronary heart disease is presented in several different percentage-based risk evaluations. A first risk 76*a* is as indicated by the risk point total. A second risk 76*b* is a "desirable risk", i.e. the risk associated a non-smoking, non-diabetic person of the same gender and age having optimal blood pressure (less than 120/80), LDL cholesterol of 100–129 mg/dL, and HDL cholesterol of 55 mg/dL. A third risk 76*c* is a "projected" risk to provide an age accounting balancing of risk (age typically being the single largest risk contributor as indicated in the risk factor chart). Thus, the third risk 76*c* evaluation can help provide a helpful basis for managed care assessment. A fourth risk 76*d* can also be included to provide a desirable risk at age 60 (one indicative of only age-related risk conditions). The age standard for persons under the 60 year mark can establish a more clear assessment of the risk a person with the measured values has for coronary heart disease. Advantageously, a patient may take more immediate steps to attempt to reduce the indicated exposure risk when presented with a longer-term standard reference risk.

The summary report 10" may also include a seventh segment 80 which is directed toward secondary prevention guidelines. As shown in FIG. 8, the sixth segment presents a discussion 80*a* on special risk considerations for patients with established coronary heart disease, other atherosclerotic vascular disease, or diabetes. These patients are considered to be at particularly high risk as measured by the NCEP guidelines. For patients having one or more of these conditions, the present recommendations are lipid management to reduce LDL cholesterol to under 100 mg/dL. The corresponding NMR LDL particle concentration target is 1100 nmol/L. For patients with small LDL (Pattern B) and a clustering of the supplemental risk factors 50 discussed above, it can be especially important to reach these LDL goals. Smoking cessation, increased exercise, healthy diet, and blood pressure control can also be considered important treatment goals.

Figure 9:
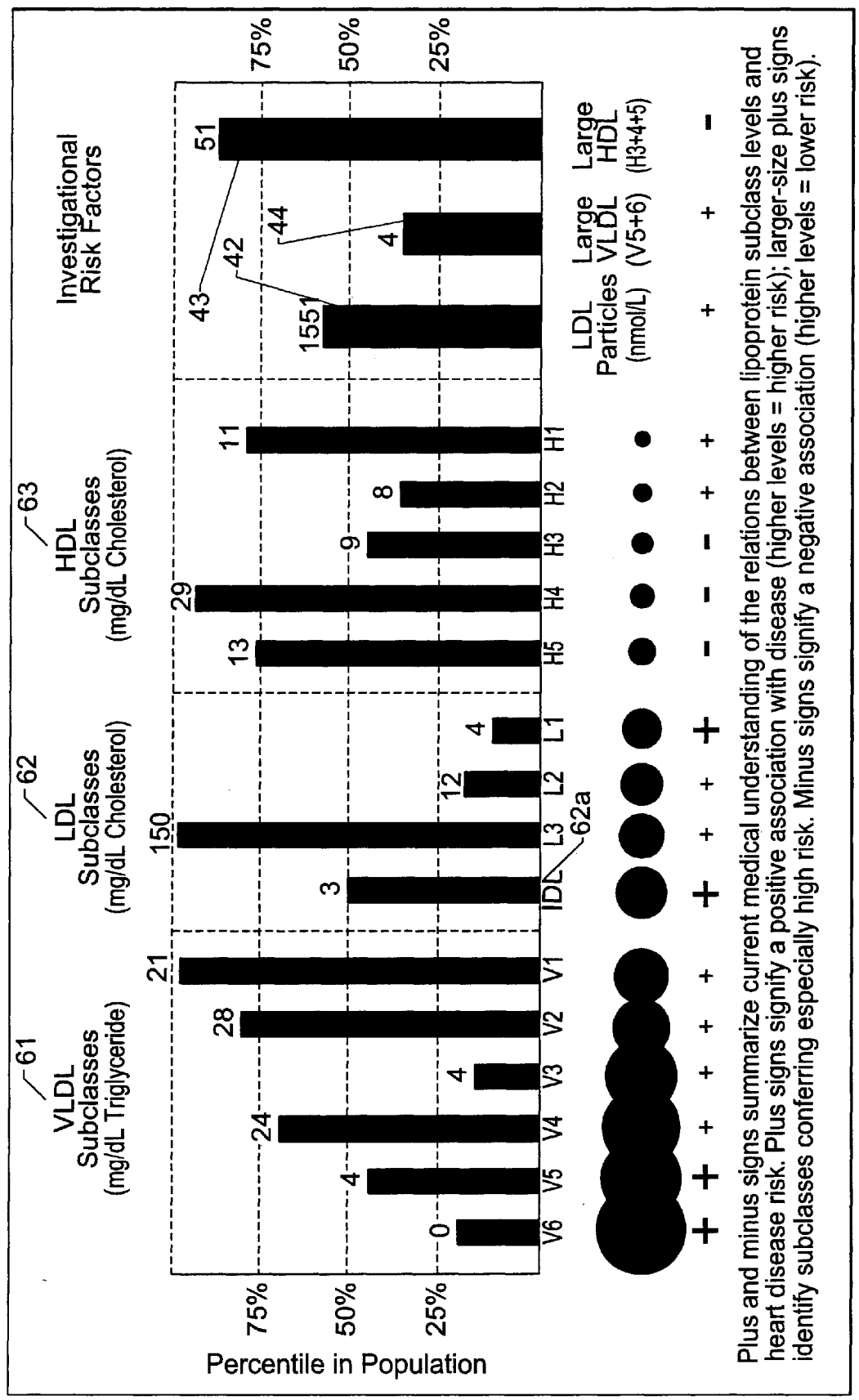
FIG. 9 is a graphic illustration of alternative embodiment of subclass information and associated positive or negative risk with coronary heart disease.

FIG. 9 graphically illustrates some of the subclass information provided by NMR analysis according to the present invention. This graph also shows the present medical understanding of the relationship between various lipoprotein subclass levels and CHD risk. The plus signs represent a positive association with disease (larger size signs indicating subclasses conferring higher risk). The higher levels indicating a higher risk. The minus signs represent a negative association, higher levels equals a lower risk. In a preferred embodiment, certain of the individual subclass information shown is combined with other subclass information shown to provide the subclass groupings described above for FIG. 6.

As discussed above, a preferred embodiment of the summary report 10 includes portions of the subclass information shown in FIG. 8 (42, 43, 44) and also includes LDL size 41. Of course, the summary report 10 can include other subclass information within the scope of this invention. Advantageously, the instant reporting system and product can be used to provide important patient-specific information in an easy to assess manner and can be generated on a mass commercial production basis. Of course, some or part of this information may be presented in a computer readable medium or hard or paper report.

Figure 10:
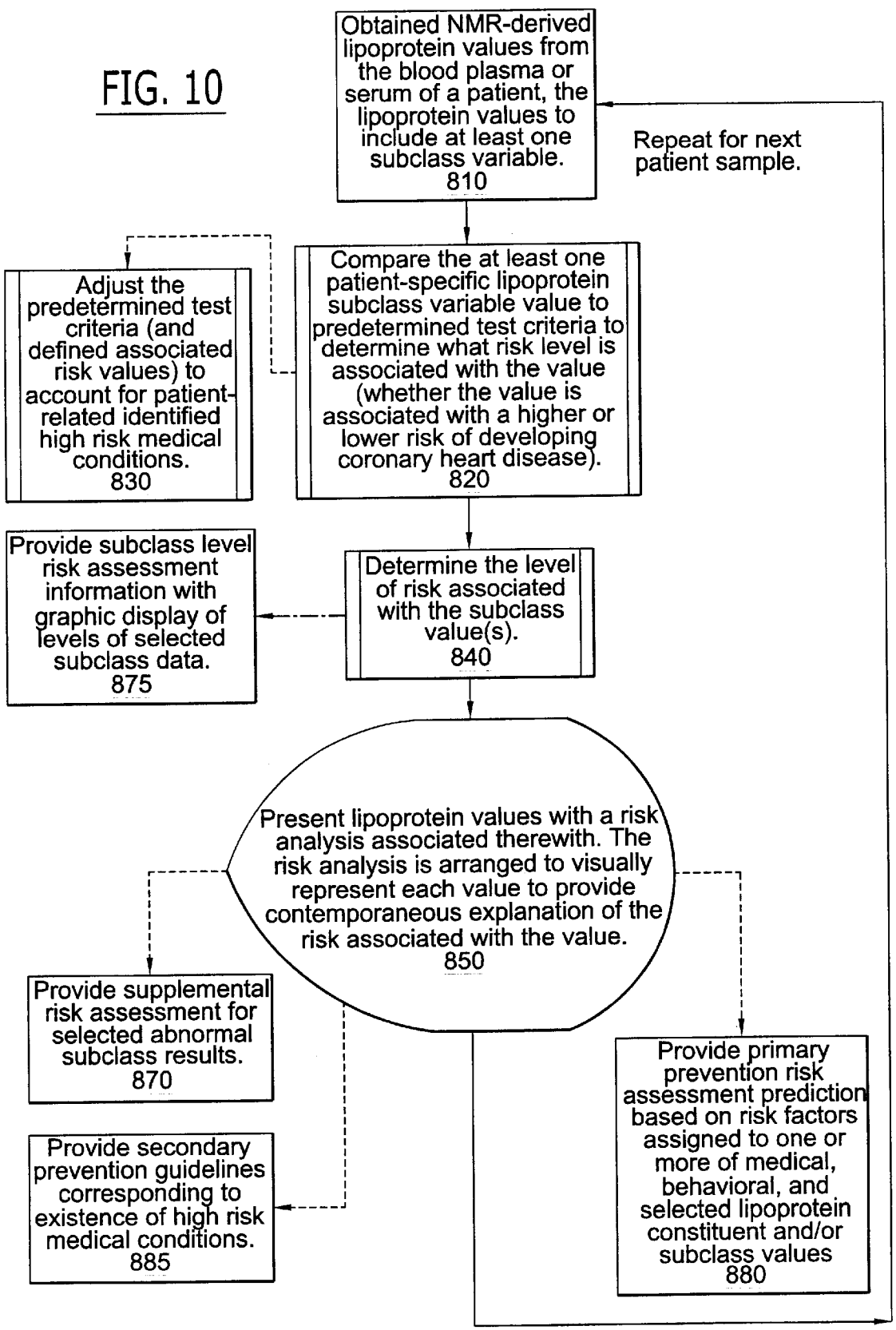
FIG. 10 is a flow chart of a method which analyzes and presents NMR derived lipoprotein information according to the present invention.

FIG. 10 illustrates a flow chart of methods, apparatus (systems) and computer program products according to the invention. It will be understood that each block of the flowchart illustration, and combinations of blocks in the flowchart illustrations, can be implemented by computer program instructions. These computer program instructions may be loaded onto a computer or other programmable data processing apparatus to produce a machine, such that the instructions which execute on the computer or other programmable data processing apparatus create means for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to produce computer implemented process such that the instructions which execute on the computer or other programmable apparatus provide steps for implementing the functions specified in the flowchart block or blocks.

Accordingly, blocks of the flowchart illustrations support combinations of means for performing the specified functions and program instruction means for performing the specified functions. It will also be understood that each block of the flowchart illustrations, and combinations of blocks in the flowchart illustrations, can be implemented by special purpose hardware-based computer systems which perform the specified functions or steps, or combinations of special purpose hardware and computer instructions.

As shown in FIG. 10, lipoprotein measurement values are obtained from a patient or subject, the values include at least one subclass value (Block 810). Preferably, an NMR spectral analysis is performed on a blood plasma sample and the lipoprotein values measured include the major lipoprotein constituents (total cholesterol, HDL, LDL, and triglycerides) as well as selected subclass values. The patient specific at least one subclass value is compared to predetermined test criteria to determine whether the value is associated with a higher or lower risk of developing coronary heart disease (Block 820). Preferably, the test criteria employed for the lipoprotein results (including the lipoprotein subclass values) correspond to a defined level of risk (low to high) of developing CHD. Preferably, the predetermined test criteria are based on scientific target "norms" or population based norms associated with higher or lower risks of CHD. These values may change over time or can be alternately identified for patients with increased secondary risk factors.

For example, if a patient has established CHD, atherosclerotic vascular disease, and/or diabetes, the "risk" criteria and values of certain constituents or subclasses may be lowered on the summary report relative to a patient without said identified diseases such that a "high" risk value may be associated with a lower value (optional Block 830). This report's ability to automatically adjust or lower the risk value based on preexisting conditions can help alert the physician that this patient is subject to stricter lipid management or protocol by visually indicating the lower risk factor value targeted for this individual. Generally, the test criteria may be set in a controlled revision software format which can be updated as NCEP guidelines or current medical analysis updates risk related information or values.

As shown in FIG. 10, the next step is to determine the level of risk associated with the lipoprotein subclass value(s) (i.e., whether it is identified as being associated with increased-risk (and/or reduced-risk) of developing coronary heart disease) (Block 840). The NMR spectroscopy measured lipoprotein results are presented with a risk category associated with the measured result visually enhanced in a two-dimensional window for easy recognition thereof (Block 850). The two-dimensional window can be a display section on a computer screen, display monitor, or electronic or hard copy or a commercial report portion or segment. Advantageously, the customized display or report can be automatically generated or mass produced such as at a commercial facility or laboratory. As shown in FIG. 1, it is preferred that each of the risk analysis information associated with the measured value be presented such that the "high" or elevated risk information is visually enhanced and aligned along one side (the same side as the other risk information for the other values) of the report or display.

Optionally, as indicated by Blocks 870, 875, 880 and 885, additional risk assessment information can also be provided. For example, a supplemental risk assessment for selected abnormal or higher risk subclass results can be provided (Block 870). This supplemental risk assessment can customize the report to provide more detailed information regarding selected or grouped subclass variables (such as LDL size or particles, large HDL, and/or large VLDL triglycerides, or atherogenic dyslipidemia). Similarly, a subclass level risk assessment can provide a graphic and textual breakdown of certain subclass groupings or selected subclass data (Block 875).

Alternatively, or additionally, a primary prevention risk assessment prediction assessment can be provided based on risk factors assigned to one or more of behavioral, medical, and/or selected lipoprotein measured constituent and/or subclass values (Block 880). As another alternative or addition, a secondary prevention guideline corresponding to recognition of the patient's diagnosis with certain high-risk medical conditions can be provided (Block 885).

Preferably, the method of the instant invention subdivides the major lipoprotein constituents and the LDL pattern separately into at least three risk categories each. It is also preferred that, the LDL particles 42, the large HDL value 43 and the large VLDL triglyceride value 44 are compared to a population based-norm and a line graph illustrates the actual measured result compared to the population with higher or lower levels of the measured value.

The behavioral or medical input can be electronically input or input via a user at the lab or report site (for example, at a blood depository or lab where the blood or plasma sample is taken from a patient). It is typical that an identification number (bar-coded) is assigned to the vials for tracking. Accordingly, a hard copy or electronic data can also be identified such as with the same identification number. Once received at the central processing facility or NMR spectroscopy laboratory, the electronic data can be entered into the facility computer and matched with the lipoprotein measurements, and a customized patient profile summary report can be conveniently generated (either in one or more of soft or hard copy). In one embodiment, the summary report can be encrypted and emailed in electronic format to a physician's address for contemporaneous data reporting. Of course, the patient can be identified by a "permanent" number to track trend or drug therapy or other treatment impact over time. Additionally, a data base can be kept to analyze population trends (age, location, etc., versus one or more of the identified risk factors represented by a subclass and/or constituents) to provide important indicators of the population for medical use.

In an additional preferred embodiment (shown in FIG. 11) a summary report 10''' (shown as the coronary heart disease report) is similar in some respects to the summary reports 10, 10' discussed above. In this embodiment, the second segment 30' is a lipid profile that provides lipid profile values which are determined by measuring plasma lipoprotein levels directly by NMR, then converting concentrations to cholesterol or triglyceride units assuming that each lipoprotein has a normal lipid composition as will be appreciated by one of skill in the art. For most patients, NMR and standard lipid panel values will closely agree. Patients with certain metabolic abnormalities or elevated triglycerides may have cholesterol-depleted LDL. In these cases LDL concentrations determined by NMR may likely be higher than those inferred by conventional or standard LDL cholesterol tests.

In this embodiment, the lipid profile segment 30' includes total cholesterol 31, LDL concentration 32' (cholesterol equivalents), HDL concentration 33'(cholesterol equivalents), and triglycerides 34. Again, each of the associated values 31a', 32a', 33a', and 34a' are accentuated such as by positioning them in aligned order in a respective adjacent box 31b, 32b, 33b, and 34b, respectively. Further, each of the values is preferably horizontally aligned with at least three risk categories 36, the risk category associated with the determined value being accentuated for ease of reference as discussed above. Preferably, the risk categories are predetermined to correspond to the current NCEP risk categories. For example, "high" risk category generally represents a value which is >80% of the population. Similarly, the intermediate or borderline risk range is above 50% and 80% or below, while the desirable risk range is 50% or below.

As shown, it is also preferred that the LDL concentration 32' include four risk categories, the fourth 36d' being an "optimal" value for secondary prevention (preferably set to a target value which is at a value of 20% or below the general population). This secondary prevention guideline is directed toward patients with established coronary heart disease, diabetes, or other atherosclerotic diseases as discussed above. Thus, this secondary guideline or "optimal" risk visual illustration can remind a treating physician of the reduced target value and can also facilitate a visible reminder for the patient, each of which can keep the secondary reduction target in the forefront of patient counseling thereby facilitating ongoing monitoring and reinforcing the importance of aggressive therapy (behavioral changes or other remediation) for a high-risk patient. This optimal box 36d' can be automatically accentuated in "red-line" or other accent as appropriate (such as via patient history data input) to remind the patient and/or physician that the patient is identified as a patient meeting the criteria for this target value reduction. Thus, for example, for a patient with diabetes, the LDL concentration risk categories 36 may bold or accent two-risk boxes, the "optimal" box with no value (for cases where a patient's result is above this value) and the actual risk box indicating the patient's actual value (not shown). Alternatively, the optimal box 36d' can be programmed in the computer generated report to be suppressed on a non-relevant patient's report (also not shown).

As is also shown in FIG. 11, the report 10''' preferably also includes a third segment 40' which is a subclass profile providing predetermined lipoprotein constituent results. As shown, the subclass profile includes, in longitudinal serial order, LDL particles 42', LDL size 41', large HDL (cholesterol) 43', and large VLDL (triglyceride) 44'.

Preferably, this subclass profile segment 40' is configured to mirror the lipid profile (second segment 30') listed constituent order (for easier cross-reference). Thus, as shown, a patient with a borderline reading on the LDL concentration value 32' (borderline risk) can then refer to the below listed subclass profile and note that the NMR measurement breakdown of the LDL concentration value 32a' really indicates that he or she is high risk both in LDL particles 42' and LDL size 41'. Similarly, the HDL concentration 33' referenced to the large HDL cholesterol 43' indicates a good correspondence (the large HDL being less than 18). Again, the risk categories for LDL particle concentration categories in the subclass profile 40' are set to correspond to the NCEP risk categories for LDL cholesterol (on a percentile equivalence basis) and can provide a constructive alternate target for therapy consideration or monitoring purposes (preferably, the risk percentages for each of the categories are about as shown, i.e., optimal 20%, desirable 50%, borderline/intermediate 80% or below (and above 50%), and high risk as above 80% of the population based on the Framingham study discussed above. The large HDL is the protective component of HDL and levels below the $20^{th}$ percentile (less than about 18 mg/dL) indicate higher risk (positive risk factor) while levels above the $80^{th}$ percentile (greater than about 42 mg/dL) indicate lower risk (negative risk factor). Elevations of large VLDL are related to delayed chylomicron clearance and higher CHD risk, and preferably, values above the $80^{th}$ percentile (greater than about 33 mg/dL) define the "higher-risk" category. FIG. 11A illustrates the summary report 10''' with a modified subclass profile 401. As shown, the LDL particle constituent has been labeled "LDL Particle Concentration" 42" and the adjacent text block 402 includes values associated with the particular percentile reference.

In contrast to the first embodiment discussed above, these summary reports 10''' present the subclass profile as a segmented risk analysis presentation format 146 (rather than a risk percentage continuum). Preferably, the segment format 146 is configured to mirror that of the lipid profile 30'. That is, the risk characterization includes the same number of risk categories with the increased, positive, or high-risk category all being positioned to one side of the presentation format. Thus, a patient or physician can readily discern the risk category associated with the NMR results (preferably, the high-risk categories are all aligned along the right hand side of the report). As for the lipid profile section 30', the results are preferably presented in a visually enhanced format, with each of the specific lipoprotein results 42a', 41a', 43a', and 44a' being presented in a box 42b', 41b', 43b', and 44b'.

Stated differently, it is readily apparent at a glance that the patient with the NMR measurements provided in FIGS. 11 or 11A, has a high-risk subclass profile 40' but only a single positive risk factor associated with the lipid profile panel 30'. In practice, without a NMR subclass profile, a patient with this type of lipid profile may have been overlooked as a candidate for further review or potential behavior altering counseling (or even drug therapy) because of the number of borderline lipid measurement results. Preferably, as stated above, the actual numerical result is presented alongside the lipoprotein constituent while the risk categories associated therewith are horizontally oriented with the risk associated with the actual numerical result highlighted to indicate the risk level associated with that lipoprotein result.

FIG. 12 illustrates a preferred embodiment of a technical report 100 associated with NMR measured lipoprotein constituents. In order to provide a more representative indication of a patient's risk, it is desirable to provide an automatically (or semi-automatically) computer generated coronary heart disease (CHD) risk assessment module 150 as a portion of the lipid panel analysis (or even as a separate evaluative report). Preferably, the CHD risk assessment module includes two key identifiers 151, 152. The first key identifier 151 is analyzing whether the patient's LDL particle number is elevated compared to a predetermined level. Preferably, the predetermined elevated level is set at a value which is approximately equivalent to the upper 50% of the population (greater than about 1400 nmol/L). The module 150 also preferably includes the relevant risk test measurement positioned adjacent to the particular constituent 151a, 153a, 154a, 155a. This elevated LDL particle number 151 is a key identifier of coronary heart disease risk, and indeed, may be the single best indicator of LDL-associated CHD risk. See Generally, Lamarche et al., Circulation, 1996; 94:273–278. Of course, the "elevated" target value could be set at above 50%.

The second key identifier 152 is termed "atherogenic dyslipidemia". As used herein, the term "atherogenic dyslipidemia" refers to an increased risk of CHD based on a clustering or confluence of NMR measured lipoprotein constituent or subclass abnormalities. Preferably, the presence or absence of atherogenic dyslipidemia is determined based on a predetermined level of at least three different NMR lipoprotein subclass or constituent values. In the past, the presence of elevated triglycerides has been used as a proxy to indicate the atherogenic dyslipidemia condition while plasma apo B protein level measurement techniques have been used to estimate the number of LDL particles. However, and advantageously, the NMR based lipoprotein measurements can provide more detailed, easier, and commercially reproducible lipoprotein component measurements. Using certain of these NMR component measurements individually (such as the determination of an elevated number of LDL particles) and in combination (to determine the presence of a clustering of abnormalities) can, thus, provide an easier and more reliable determination and assessment of a patient's risk for CHD.

In a preferred embodiment, the positive or affirmative match to test criteria for at least two of the three selected-lipoprotein subclass or constituent values results in a designation of atherogenic dyslipidemia. This NMR-based lipoprotein atherogenic dyslipidemia test criteria 152 can provide a more reliable analysis of a patient's risk for CHD over isolated component values. For example, a patient's individual or component constituent or subclass values may all be insufficient to determine or provide a reliable indication of increased risk of CHD, but a clustering of certain abnormal conditions or results can indicate a higher-risk metabolic condition. Indeed, patients with a clustering of the lipoprotein subclass abnormalities shown (small LDL 153, low level of HDL 154, and elevated level of large VLDL 155) are at higher risk of CHD when risk identifier 151 is indicated, i.e., when LDL particle numbers are elevated. Thus, the present invention uses positive matches for two or more of the plurality of lipoprotein constituent values listed to indicate the presence of the higher-risk metabolic condition.

The CHD atherogenic dyslipidemia assessment preferably includes a test for small LDL 153 and low levels of large HDL 154. Small LDL 153 (Pattern B) is a hallmark of atherogenic dyslipidemia and confers about a three-fold higher risk compared to the large LDL trait (Pattern A). Evidence suggests that small LDL particles may be inherently more atherogenic than large LDL. An indication of a low level of large HDL 154 has a positive association with CHD. A low level of large HDL means a NMR derived value which is below the 50%, and more preferably means the value is below 35% (less than about 23 mg/dL). That is, only the larger HDL subclasses appear to be protective, whereas small HDL is positively associated with CHD. Therefore, large HDL, rather than total HDL cholesterol, may be a more sensitive risk factor and, indeed, an independently predictive marker for CHD in addition to being a factor which can assist in the determination of atherogenic dyslipidemia.

Similarly, the CHD atherogenic dyslipidemia risk assessment preferably includes a test for elevated levels of large VLDL 155. Elevated levels of large, triglyceride-rich VLDL particles have been associated with the severity of CAD, independently of plasma triglycerides. High concentrations of large VLDL in fasting plasma are a marker for delayed chylomicron clearance (postprandial lipemia). "Elevated" for VLDL means the value is in the upper $50^{th}$ percentile, and preferably means above about the $65^{th}$ percentile (greater than about 17 mg/dL) or such as in the upper 33%.

Additional or alternative lipoprotein subclass or constituent parameters may also be used as a test parameter for atherogenic dyslipidemia. Similarly, the percentile-based values are preferably as shown but may also be other values. For example, these values can be altered to reflect contemporary guidelines by the NCEP or other health organization, statistically valid tests or studies, scientific or empirical data and the like. As will be appreciated by one of skill in the art, the percentile values are preferably set to reflect an acceptable sensitivity/specificity test result. FIG. 12A illustrates another embodiment with a modified risk assessment module 150'. As shown, the first key risk factor 151 is labeled "Elevated LDL Particle Conc.[entration]". The module 150' includes a modified test criteria over that in FIG. 12 and also includes values rather than percentile references. The text in certain of the associated risk analysis is also modified from FIG. 12.

The population percentile values described herein are from NMR data obtained from analysis of 3,437 subjects in the Framingham Offspring study. However, the present invention is not limited thereto. As noted above, these values may change over time, or other percentiles or values may be used.

As discussed for the report of FIG. 2, the reports 100 shown in FIGS. 12 and 12A also preferably include a subclass graphic analysis segment 60' with grouped subclass data. As shown, the HDL results give a visual representation of the disparity of small (bad or harmful) HDL to the large (good) HDL. This patient is above the $75^{th}$ percentile in (bad) small HDL and indeed has a positive risk indication across the spectrum of the lipoprotein subclass values (ignoring the low level of large HDL). Thus, this patient's overall conventional lipid profile is not reflective of his or her actual risk.

FIG. 13 illustrates a hybrid summary report 110 with a subclass profile segment as shown in FIG. 11A and a CHD risk assessment module as shown in FIG. 12A. This report 110 provides an easy to read single page overview or summary of the most relevant heart-specific test measurement results.

Figure 14:
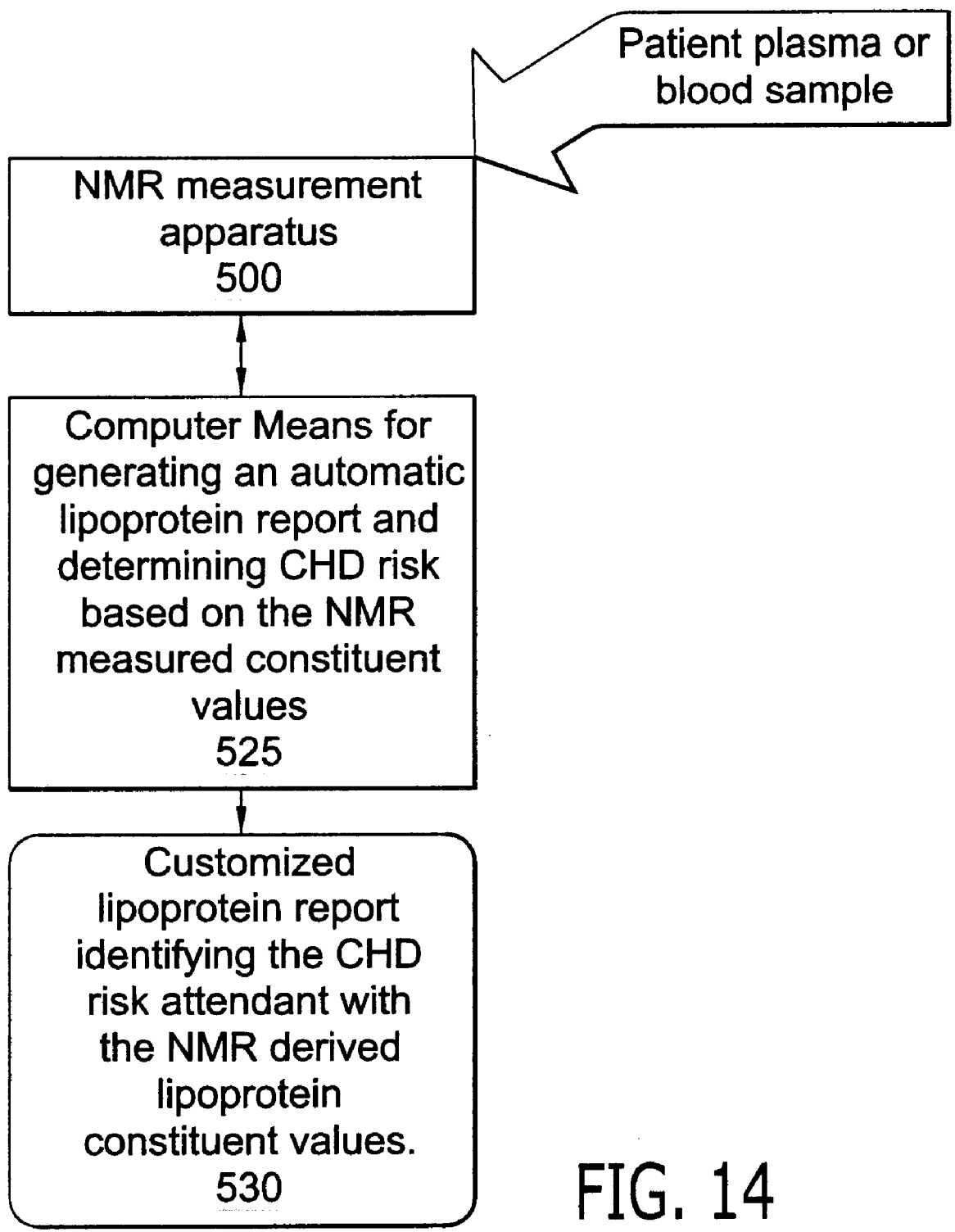
FIG. 14 schematically illustrates a system according to one embodiment of the present invention.

FIG. 14 schematically illustrates a system according to one embodiment of the present invention. As shown, the system includes an NMR measurement apparatus 500 for measuring the lipoprotein constituents of a patient's blood or plasma sample. A suitable method for determining the lipoprotein constituents is disclosed in U.S. Pat. No. 4,933,844 to Otvos, entitled "*Measurement of Blood Lipoprotein Constituents by Analysis of Data Acquired From an NMR*

*Spectrometer*" and U.S. Pat. No. 5,343,389 to Otvos, entitled "*Method and Apparatus for Measuring Classes and Subclasses of Lipoproteins*", incorporated by reference above. The system also includes a computer means for generating an automatic lipoprotein report and determining CHD risk based on the NMR measured constituent values 525. The computer means then generates a customized lipoprotein report which includes information identifying the CHD risk attendant with the NMR derived lipoprotein constituent values 530. Preferably, the system is operably associated with a peripheral device such as another computer or internet or printer so as to transmit and print or display the customized report.

As will be appreciated by one of skill in the art, the present invention may be embodied as a method, data processing system, hard copy two-dimensional printed material report, computer screen display, or computer program product. Accordingly, the present invention may take the form of an entirely hardware embodiment, an entirely software embodiment or an embodiment which combines software and hardware aspects. Furthermore, the present invention may take the form of a computer program product on a computer readable storage medium having computer readable program code means embodied in the medium. Any suitable computer readable medium may be utilized including for example, hard disks, CD-ROMs, optical storage devices, or magnetic storage devices.

A portion of the disclosure of this patent document contains material which is subject to copyright protection. The copyright owner, LipoMed, Inc., of Raleigh, N.C., has no objection to the facsimile by anyone of the patent document or the patent disclosure, as it appears in the Patent and Trademark Office patent file or records, but otherwise reserves all rights whatsoever.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed:

1. A computer program product for automatically generating personalized lipoprotein-based information for a plurality of subjects, the computer program product comprising:
   a computer readable storage medium having computer readable program code embodied in said medium, said computer-readable program code comprising:
   computer readable program code for generating lipoprotein measurement values for a patient's blood and/or plasma sample, the lipoprotein measurement values including a plurality of lipoprotein subclass variable measurements, including at least two of: LDL size, LDL concentration, large HDL concentration, and large VLDL concentration;
   computer readable program code for comparing the plurality of patient lipoprotein subclass variable values with respective predetermined test criteria for determining whether the subclass variable values are associated with a higher lower risk of developing coronary heart disease;
   computer program code for evaluating the lipoprotein measurement values and generating a reduced target value or values for what represents an optimal or low risk value for selected lipoprotein constituents to provide a patient-specific treatment guideline based on the presence of predetermined risk criteria; and
   computer readable program code for automatically generating personalized lipoprotein-based reports for a plurality of patients, wherein the computer program code for generating the report includes computer program code for generating a plurality of risk analysis portions representing lower to higher degrees of risk therein, one for each measured lipoprotein subclass, so that a respective one risk analysis portion is aligned adjacent the corresponding measured subclass lipoprotein value, each of the respective risk analysis portions visually indicating when there is a higher risk of coronary heart disease for the measured value by displaying and/or printing the corresponding degree of risk associated with the measured value within a respective risk analysis portion in a visually accentuated manner to thereby provide a contemporaneous reference guideline for interpretation of the measured value, wherein at least one of the risk analysis portions comprises a plurality of discrete horizontal boxes, each representing a predetermined degree of risk and/or a positive or negative risk association, and wherein the computer readable program code for generating the risk analysis portions comprises computer program code that generates one box with a color enhanced border that is in a different color from the other discrete boxes in that risk analysis portion.

2. A computer program product according to claim 1, further comprising computer readable program code for comparing a plurality of the lipoprotein measurement values to predetermined test criteria to determine the presence of an increased risk of metabolic syndrome or atherogenic dyslipidemia.

3. A computer program product according to claim 1, wherein the computer readable program code for generating lipoprotein measurement values for a patient's blood sample comprises computer program code for obtaining NMR-based lipoprotein measurements.

4. A computer program product according to claim 1, wherein the lipoprotein measurement values include NMR equivalents of the major lipoprotein constituents of total cholesterol as well as the plurality of lipoprotein subclass constituents, wherein the computer program code is configured to arrange the total cholesterol values above the subclass constituent values in the report, and wherein the major lipoprotein constituents include LDL concentration in cholesterol equivalents, HDL concentration in cholesterol equivalents, and triglycerides.

5. A computer program product according to claim 1 wherein the at least two subclass values comprise each of the subclass values for LDL size, LDL concentration, large HDL concentration, and large VLDL concentration.

6. A computer program product according to claim 1, wherein the computer program code for generating the reports comprises computer program code for generating linear horizontal line graphs representing lower to higher degrees of coronary heart disease risk in a plurality of the subclass risk analysis portions so that the relative risk associated with the measured value is graphically represented according to predefined risk criteria associated with statistical data for the general population to establish for the respective subclass values a relative continuum of low to high risk to visibly indicate the level of risk associated therewith.

7. A computer program product according to claim 1, wherein the computer program code for generating the reports includes computer program code for:

analyzing the lipoprotein measurements and providing at least three different lipoprotein result summary segments, a lipid profile segment and a lipoprotein-subclass profile segment, and a separate metabolic abnormality summary segment, wherein the lipid profile segment presents values for total cholesterol, LDL cholesterol, HDL cholesterol, and Triglycerides, wherein the subclass profile segment presents the results of the lipoprotein measurements for the level and size of LDL particles, the level of large HDL, and the level of large VLDL, and wherein the metabolic abnormality summary segment presents the patient's risk identification for having a metabolic abnormality.

8. A computer program product according to claim 1, wherein the computer readable program code for generating the reports comprises computer program code for arranging the measured lipoprotein values such that the lipoprotein measurement values are substantially vertically aligned relative to one another, and wherein the computer program code for generating the risk analysis portion for LDL particle size generates three discrete boxed segments of risk categories, one associated with lower risk for Pattern A, one associated with intermediate risk for Pattern AB, and one associated with higher risk for Pattern B.

9. A computer program product according to claim 1, wherein the computer program code for generating lipoprotein measurement values for a patient's blood sample comprises computer program code for obtaining NMR-based lipoprotein measurements, and wherein the computer readable program code for comparing the NMR-based lipoprotein measurement values to predetermined test criteria to determine the presence of atherogenic dyslipidemia includes computer program code for comparing the measurement values to predetermined test criteria to determine the presence of small LDL, a low level of large HDL, and an elevated level of large VLDL, whereby the determination is made based on the positive test criteria match of at least two of the conditions.

10. A computer program product according to claim 1, further comprising computer program code for monitoring the patient's lipoprotein measurements over time by automatically comparing data successive personalized patient reports from respective selected patients to identify a decrease, an increase or stability in at least one selected lipoprotein subclass constituent value over time to thereby monitor the trend or impact of drug therapy or other treatment.

11. A computer program product according to claim 1, wherein the computer code for evaluating processes data associated with selected parameters from both the patient's medical and behavioral history.

12. A computer program product according to claim 1, further comprising computer program code for adjusting the predetermined test criteria as well as the associated risk analysis portions for a particular patient relative to the general population based upon the existence of or susceptibility to an identified high-risk medical condition in the patient.

13. A computer program product according to claim 1, wherein the measured lipoprotein subclass measured values are presented in columnated numerical format as a quantitative number adjacent a corresponding columnated textual label identifying the corresponding subclass variable value.

14. A computer program product according to claim 1, further comprising computer program code for electronically generating the report and transmitting the report via email to a physician or clinic.

15. A computer program product according to claim 2, wherein the computer program code for generating the report comprises computer program code for generating a selectable box adjacent parameters associated with an increased risk of metabolic syndrome or atherogenic dyslipidemia and visually accentuating the box when the increased risk is determined to be present.

16. A computer program product according to claim 2, wherein the computer readable program code for generating the risk analysis portions in the reports includes computer readable program code for presenting a plurality of the measured lipoprotein subclass values as a series of horizontally extending line graphs which graphically represents the subclass value in a relative continuum of low to high risk, the continuum of low to high risk being defined according to predefined risk criteria associated with statistical data for the general population.

17. A computer program product according to claim 11, wherein the computer program code evaluates and identifies data that defines whether the patient is diabetic.

18. A computer program product according to claim 11, wherein the computer program code processes data in the patient's history to determine whether the patient has been diagnosed with CHD.

19. A computer program product for providing patient specific NMR-measured lipoprotein information, the computer program product comprising:

a computer readable storage medium having computer readable program code means embodied in said medium, said computer-readable program code means comprising:

computer readable program code for obtaining NMR-measurements for a plurality of lipoprotein subclass constituents including at least LDL particle size, LDL concentration, and large HDL concentration;

computer readable program code for determining a coronary heart disease risk level associated with each of the plurality of NMR-measured lipoprotein subclass measurements;

computer program code for evaluating the lipoprotein measurement values and generating a reduced target value or values for what represents an optimal or low risk value for selected lipoprotein constituents to provide a patient-specific treatment guideline based on the presence of predetermined risk criteria; and computer readable program code for automatically generating a lipoprotein report for a plurality of patients with data corresponding to patient specific NMR-measured lipoprotein subclasses, the computer readable program code for generating the reports including computer readable program code for generating, for each reported measured subclass value, an adjacently positioned associated risk analysis portion according to predetermined risk criteria associated with the measured subclass value, with the risk for a measured value to be represented in the risk analysis portion in at least one of (i) a color-accentuated manner; (b) a different selected font relative to adjacent portions of the report; (c) bolded; (d) italicized; (e) circled; (f) boxed; (g) underlined; and (h) highlighted to thereby provide a contemporaneous reference guideline for interpretation of the measured lipoprotein subclass value.

20. A computer program product according to claim 19, wherein the computer readable program code means for generating the risk analysis portion presents the LDL particle size value as one of: Pattern A corresponding to lower risk, Pattern B corresponding to higher risk, and Pattern AB corresponding to an intermediate risk; and wherein said LDL subclass value is identified in said risk analysis portion by visually enhancing the specified pattern associated with the patient-specific LDL subclass value, and wherein, for at least one risk analysis portion, the computer program code for generating the report generates a plurality of spaced apart predetermined risk segments having an associated border, the risk segments corresponding to lower or negative to higher or positive degrees of risk, and wherein the computer program code causes the border of the risk segment associated with the measured subclass value to be drawn in a color-accentuated manner.

21. A computer program product according to claim 19, further comprising computer program code for evaluating the lipoprotein measurement values to adjust and present a patient-specific goal that is more conservative than for the general population for certain of the measured lipoprotein values based on the presence or absence of predetermined risk criteria.

22. A computer program product according to claim 19, further comprising computer program code for electronically generating the report and transmitting the report via email to a physician.

23. A computer program product according to claim 19, wherein the NMR-measured values include levels of the major lipoprotein constituents of total cholesterol, LDL cholesterol, HDL cholesterol, and triglycerides, and the subclass lipoprotein values associated with LDL size, the level of LDL particles, the level of large HDL cholesterol, and the level of large VLDL.

24. A computer program product according to claim 19, further comprising computer program code for adjusting the predetermined risk criteria in the risk analysis portion used to estimate the defined risk associated with the risk analysis portions based upon the existence of or susceptibility to an identified high-risk medical condition in the patient relative to the predetermined risk criteria used for the general population.

25. A computer program product according to claim 19, wherein the plurality of NMR-measured lipoprotein subclass variable values further includes data corresponding to large VLDL concentration.

26. A computer program product according to claim 19, further comprising computer readable program code for defining predetermined test criteria that define an increased risk of metabolic syndrome and/or atherogenic dyslipidemia and computer readable program code for comparing a plurality of the NMR-measured lipoprotein values to the predetermined test criteria to determine the presence of an increased risk of metabolic syndrome or atherogenic dyslipidemia.

27. A computer program product according to claim 19, further comprising computer program code for monitoring the patient's lipoprotein measurements over time by automatically comparing data successive personalized patient reports from respective selected patients to identify a decrease, an increase or stability in at least one selected lipoprotein subclass constituent value over time to thereby monitor the trend or impact of drug therapy or other treatment on the lipoprotein values.

28. A computer program product according to claim 19, further comprising computer program code for adjusting the predetermined risk criteria and corresponding levels of risk associated with the measured lipoprotein subclass values relative to the general population as presented in the associated risk analysis portions of the display format based upon the existence of or an identified susceptibility to an at-risk medical condition of the patient.

29. A computer program product according to claim 21, wherein the computer code for evaluating processes data from selected parameters input from both the patient's medical and behavioral history.

30. A computer program product according to claim 21, further comprising computer program code for evaluating data that identifies whether the patient is diabetic.

31. A computer program product according to claim 21, wherein the computer program code for evaluating processes data in a patient history electronic file to identify whether the patient has already been diagnosed with CHD.

32. A computer program product according to claim 2, wherein the computer program code for generating the report includes program code for visually accentuating at least one box generated in a risk assessment panel that is separate from the risk analysis portions of the lipoprotein subclass constituent values when an increased risk of metabolic syndrome or atherogenic dyslipidemia is determined to be present.

33. A computer program product for providing patient specific NMR-measured lipoprotein information, the computer program product comprising:
  a computer readable storage medium having computer readable program code means embodied in said medium, said computer-readable program code means comprising:
    computer readable program code for obtaining NMR-measured measurements for a plurality of lipoprotein subclass constituents including at least LDL particle size, LDL concentration, and large HDL concentration;
    computer readable program code for determining a coronary heart disease risk level associated with each of the plurality of NMR-measured lipoprotein subclass measurements;
    computer program code for evaluating the lipoprotein measurement values and generating a reduced target value or values for what represents an optimal or low risk value for selected lipoprotein constituents to provide a patient-specific treatment guideline based on the presence of predetermined risk criteria; and
    computer readable program code for automatically generating a lipoprotein report for a plurality of patients with data corresponding to patient specific NMR-measured lipoprotein subclasses, the computer readable program code for generating the reports including computer readable program code for generating, for each reported measured subclass value, an adjacently positioned associated risk analysis portion that visually accentuates when there is an increased risk of coronary heart disease associated with the respective lipoprotein subclass measurement to thereby provide a contemporaneous reference guideline for interpretation of the measured lipoprotein subclass value, wherein the computer readable program code means for generating the risk analysis portion presents the LDL particle size value as one of: Pattern A corresponding to lower risk, Pattern B corresponding to higher risk, and Pattern AB corresponding to an intermediate risk; and wherein said LDL subclass value is identified in said risk analysis portion by visually enhancing the specified pattern associated with the patient-specific LDL subclass value, and wherein the computer readable program code for generating the risk analysis portion includes computer readable program code for presenting each of a plurality of the measured subclass values as a horizontally extending linear bar graph which graphically represents the subclass value relative to a continuum of low to high risk, the continuum of low to high risk being defined according to predefined risk criteria associated with statistical data for the general population.

34. A computer program product for automatically generating personalized lipoprotein-based assessed risk of coronary heart disease information for a plurality of subjects, the computer program product comprising:

a computer readable storage medium having computer readable program code embodied in said medium, said computer-readable program code comprising:

computer readable program code for generating NMR-based lipoprotein measurement values for a patient's blood plasma or serum sample, the NMR-based lipoprotein measurement values comprising a plurality of lipoprotein constituent values including a constituent value for LDL particle concentration;

computer readable program code for comparing the LDL particle concentration with predetermined test criteria for determining whether the LDL particle concentration is elevated;

computer readable program code for comparing a plurality of NMR-based lipoprotein subclass constituent values to predetermined test criteria associated with abnormal lipoprotein values to determine if there is a clustering of abnormal values for a plurality of different selected lipoprotein subclass constituents according to predetermined test criteria to determine the presence of a metabolic abnormality or atherogenic dyslipidemia;

computer program code for evaluating the lipoprotein measurement values and generating a reduced target value or values for what represents an optimal or low risk value for selected lipoprotein constituents to provide a patient-specific treatment guideline based on the presence of predetermined risk criteria; and computer readable program code for assessing a patient's risk of coronary heart disease based on the presence of at least one of an elevated LDL particle concentration and/or the metabolic abnormality or atherogenic dyslipidemia.

35. A computer program product according to claim 34, wherein the NMR based lipoprotein constituent values include the major lipoprotein constituents of total cholesterol, LDL concentration in cholesterol equivalents, HDL concentration in cholesterol equivalents, and triglycerides.

36. A computer program product according to claim 34, wherein the computer program code for comparing the plurality of NMR-based lipoprotein subclass constituent values to predetermined test criteria associated with abnormal lipoprotein values to determine if a clustering of abnormal values exist to determine the presence of a metabolic abnormality or atherogenic dyslipidemia does not consider NMR based lipoprotein constituent values for LDL particle concentration or LDL-cholesterol.

37. A computer program product for automatically generating personalized lipoprotein-based assessed risk of coronary heart disease information for a plurality of subjects, the computer program product comprising:

a computer readable storage medium having computer readable program code embodied in said medium, said computer-readable program code comprising:

computer readable program code for generating NMR-based lipoprotein measurement values for a patient's blood plasma or serum sample, the NMR-based lipoprotein measurement values comprising a plurality of lipoprotein constituent values including a constituent value for LDL particle concentration;

computer readable program code for comparing the LDL particle concentration with predetermined test criteria for determining whether the LDL particle concentration is elevated;

computer readable program code for comparing a plurality of NMR-based lipoprotein subclass constituent values to predetermined test criteria associated with abnormal lipoprotein values exist to determine if a clustering of abnormal values exist to determine the presence of a metabolic abnormality or atherogenic dyslipidemia;

computer readable program code for assessing a patient's risk of coronary heart disease based on the presence of at least one of an elevated LDL particle concentration and/or the metabolic abnormality or atherogenic dyslipidemia; and computer program code for automatically generating a report of the risk assessment for each patient sample, the computer program code for generating the report including computer program code for:

(a) arranging each of the obtained lipoprotein subclass constituent values in a viewable format which positions the lipoprotein subclass constituent values as a quantified number adjacent to a corresponding risk analysis portion such that a respective risk analysis portion for each lipoprotein subclass constituent value is positioned in side by side alignment with the corresponding lipoprotein subclass constituent value to act as a contemporaneous guide, the risk analysis portion having a plurality of segments a respective one of which characterizes the quantified lipoprotein subclass constituent value's determined risk level;

(b) displaying the NMR-measured subclass constituent risk result corresponding to the actual constituent value within the respective risk analysis portion such that the risk associated with the lipoprotein constituent value is readily apparent; and (c) providing a metabolic abnormality or metabolic syndrome and/or atherogenic dyslipidemia summary identifying whether a clustering of abnormal measured lipoprotein subclass constituent values for selected different lipoprotein subclass constituents exists according to predetermined test criteria and indicating which of the plurality of the measured lipoprotein subclass constituent values are abnormal.

38. A computer program product according to claim 37, further comprising computer program code for defining a target or optimal value that is a reduced target value set at about or below about a $20^{th}$ percentile value for at-risk patients relative to the general population.

39. A computer program product according to claim 38, wherein the computer program code for generating the report includes computer program code for:
providing at least three different result summary segments, a lipid profile segment and a lipoprotein-subclass profile segment, and a separate metabolic abnormality summary segment, wherein the lipid profile segment presents the results of the lipoprotein measurements for total cholesterol, LDL concentration cholesterol equivalent, HDL concentration cholesterol equivalent, and Triglycerides, wherein the subclass profile segment presents the results of the lipoprotein measurements for concentration and size of LDL particles, large HDL, and large VLDL, and wherein the metabolic abnormality summary segment presents the patient's risk identification of a metabolic abnormality.

40. A computer program product according to claim 37, wherein the computer program code further associates the lipoprotein constituent values for LDL particle concentration number, the level of large HDL, and the level of large VLDL triglyceride with a risk analysis portion which includes at least three discrete segments, and wherein the computer program code that generates the discrete segments identifies the respective measured lipoprotein constituent value as having a particular risk level associated therewith.

41. A computer program product according to claim 37, further comprising computer program code for adjusting the predetermined risk criteria and corresponding levels of risk representing an increased risk and/or optimal or low risk level relative to the general population based upon the existence of or susceptibility to an identified high-risk medical condition in the patient.

42. A computer program product according to claim 40, wherein the computer program code for generating the at least three discrete segments define a first desirable, negative, or low risk segment, a second borderline or intermediate risk segment, and a third positive, increased and/or high risk segment.

43. A computer program product according to claim 40, wherein the computer program code for generating the discrete segments arranges and aligns the risk analysis portions to present the higher risk segments in a substantially vertically aligned manner, and wherein the computer program product further comprises computer program code for arranging the measured values for the lipoprotein constituents within respective boxes, each box disposed proximate to and laterally offset from its corresponding discrete segments of its respective risk analysis portion such that the measured values are arranged in vertical alignment proximate one side of the report and the risk analysis portions are arranged about the opposing side of the report.

44. A computer program product for automatically generating personalized lipoprotein-based assessed risk of coronary heart disease information for a plurality of subjects, the computer program product comprising:
a computer readable storage medium having computer readable program code embodied in said medium, said computer-readable program code comprising:
computer readable program code for generating NMR-based lipoprotein measurement values for a patient's blood plasma or serum sample, the NMR-based lipoprotein measurement values comprising a plurality of lipoprotein constituent values including a constituent value for LDL particle concentration;
computer readable program code for comparing the LDL particle concentration with predetermined test criteria for determining whether the LDL particle concentration is elevated;
computer readable program code for comparing a plurality of NMR-based lipoprotein subclass constituent values to predetermined test criteria associated with abnormal lipoprotein values to determine if there is a clustering of abnormal values to determine the presence of a metabolic abnormality or atherogenic dyslipidemia; and
computer readable program code for assessing a patient's risk of coronary heart disease based on the presence of at least one of an elevated LDL particle concentration and/or the metabolic abnormality or atherogenic dyslipidemia, wherein the computer program code for assessing a patient's risk of coronary heart disease includes computer program code that identifies the presence of both an elevated LDL particle concentration and the determination of an increased risk for having the metabolic abnormality, metabolic syndrome and/or atherogenic dyslipidemia, and wherein the computer program code for comparing a plurality of NMR-based lipoprotein subclass constituent values to predetermined test criteria associated with abnormal lipoprotein values to determine if there is a clustering of abnormal values for a plurality of different selected lipoprotein subclass constituents exists to determine the presence of a metabolic abnormality or atherogenic dyslipidemia lack a LDL particle concentration value.

45. A computer program product for automatically generating personalized lipoprotein-based assessed risk of coronary heart disease information for a plurality of subjects, the computer program product comprising:
a computer readable storage medium having computer readable program code embodied in said medium, said computer-readable program code comprising:
computer readable program code for generating NMR-based lipoprotein measurement values for a patient's blood plasma or serum sample, the NMR-based lipoprotein measurement values comprising a plurality of lipoprotein constituent values including a constituent value for LDL particle concentration;
computer readable program code for comparing the LDL particle concentration with predetermined test criteria for determining whether the LDL particle concentration is elevated;
computer readable program code for comparing a plurality of NMR-based lipoprotein subclass constituent values to predetermined test criteria associated with abnormal lipoprotein values to determine if there is a clustering of abnormal values for a plurality of different selected lipoprotein subclass constituents to determine the presence of a metabolic abnormality or atherogenic dyslipidemia;
computer readable program code for assessing a patient's risk of coronary heart disease based on the presence of at least one of an elevated LDL particle concentration and/or the metabolic abnormality or atherogenic dyslipidemia; and
computer program code for evaluating the lipoprotein measurement values and generating different values or ranges of values for the predetermined risk criteria that establishes the estimated risk level for at least one selected subclass constituent relative to the general population for a patient-specific treatment guideline based on the presence of predetermined risk criteria.

46. A computer program product according to claim 45, wherein the computer program code for evaluating and generating the different values or ranges of values to provide the estimated risk level for the patient-specific treatment guideline processes data from selected parameters from both the patient's medical and behavioral history.

47. A computer program product according to claim 45, wherein the computer program code for evaluating to generate specific treatment guideline uses data that identifies whether the patient is diabetic.

48. A computer program product according to claim 45, wherein the computer program code for evaluating to generate specific treatment guideline processes data that identifies whether the patient has been diagnosed with CHD.

49. A computer program product for automatically generating personalized lipoprotein-based assessed risk of coronary heart disease information for a plurality of subjects, the computer program product comprising:

a computer readable storage medium having computer readable program code embodied in said medium, said computer-readable program code comprising:
computer readable program code for generating NMR-based lipoprotein measurement values for a patient's blood plasma or serum sample, the NMR-based lipoprotein measurement values comprising a plurality of lipoprotein constituent values including a constituent value for LDL particle concentration;

computer readable program code for comparing the LDL particle concentration with predetermined test criteria for determining whether the LDL particle concentration is elevated;

computer readable program code for comparing a plurality of NMR-based lipoprotein subclass constituent values to predetermined test criteria associated with abnormal lipoprotein values to determine if there is a clustering of abnormal values associated with a plurality of different selected lipoprotein subclass constituents to determine the presence of a metabolic abnormality, metabolic syndrome, and/or atherogenic dyslipidemia;

computer readable program code for assessing a patient's risk of coronary heart disease based on the presence of at least one of an elevated LDL particle concentration and/or the metabolic abnormality, syndrome and/or atherogenic dyslipidemia; and computer program code for electronically generating the report and transmitting the report via email to a physician.

* * * * *

UNITED STATES PATENT AND TRADEMARK OFFICE
CERTIFICATE OF CORRECTION

PATENT NO.   : 6,576,471 B2
DATED        : June 10, 2003
INVENTOR(S)  : Otvos

It is certified that error appears in the above-identified patent and that said Letters Patent is hereby corrected as shown below:

<u>Column 24,</u>
Line 27, should read as follows: -- 32. A computer program product according to claim 26 --

Signed and Sealed this

Thirteenth Day of April, 2004

JON W. DUDAS
*Acting Director of the United States Patent and Trademark Office*